United States Patent [19]
Ippoliti et al.

[11] Patent Number: 5,637,728
[45] Date of Patent: Jun. 10, 1997

[54] METAL ION BINDING MONOMER AND POLYMER

[75] Inventors: J. Thomas Ippoliti; Gary A. Mabbott, both of St. Paul, Minn.; Jeremy Hans, Madison, Wis.; Michelle Stohlmeyer, Dubuque, Iowa

[73] Assignee: Research Corporation Technologies, Inc., Tucson, Ariz.

[21] Appl. No.: 466,158

[22] Filed: Jun. 6, 1995

Related U.S. Application Data

[60] Division of Ser. No. 317,433, Oct. 3, 1994, abandoned, which is a continuation-in-part of Ser. No. 130,330, Oct. 1, 1993, Pat. No. 5,455,359.

[51] Int. Cl.⁶ .................. C07D 403/06; C07D 233/64; C07D 233/54
[52] U.S. Cl. .................... 548/314.4; 548/341.1; 548/343.1
[58] Field of Search .............. 526/262; 548/335.1, 548/341.1, 343.1, 314.4

[56] References Cited

U.S. PATENT DOCUMENTS

| | | |
|---|---|---|
| 3,288,707 | 11/1966 | Hurwitz et al. |
| 3,488,294 | 1/1970 | Annand et al. |
| 3,835,046 | 9/1974 | Restaino |
| 3,907,677 | 9/1975 | Capozza |
| 4,006,247 | 2/1977 | Panzer et al. |
| 4,007,200 | 2/1977 | Panzer et al. |
| 4,113,934 | 9/1978 | Panzer et al. |
| 4,869,838 | 9/1989 | Gorun et al. |
| 5,094,759 | 3/1992 | Mathias et al. |

FOREIGN PATENT DOCUMENTS

| | | |
|---|---|---|
| 2 164 919 | 7/1973 | Germany |
| 40 41 772 | 6/1992 | Germany |
| 40 41 773 | 6/1992 | Germany |
| 4041772 | 6/1992 | Germany |
| 42-4133 | 2/1967 | Japan |

OTHER PUBLICATIONS

Ohta et al. (1986) "Synthesis and Application of Imidazole Derivatives. Synthesis and Acyl Activation of 2-Acyl-1-Methyl-1H-Imidazoles", *Chem. Pharm. Bull.*, 34(12), 4916-4926.

D.A. Evans et al., "Bis(oxazoline) copper (II) Complexes as Chiral Catalysts for the Enantioselective Diels-Alder Reaction", *J. Am. Chem. Soc.*, vol. 115, No. 14, pp. 6460-6461 1993).

C.N.C. Drey et al., "Metal Chelates of A Bis-imidazole", *Biochemistry*, vol. 4, No. 7, pp. 1258-1263 (1965).

C.C. Tang et al., "Models for Metal Binding Sites in Zinc Enzymes. Syntheses of Tris[4(5)–imidazolyl]carbionol (4-TIC), Tris(2-imidazolyl)carbinol (2-TIC), and Related Ligands, and Studies on Metal Complex Binding Constants and Spectra", *J. Am. Chem. Soc.*, vol. 100, No. 12, pp. 3918-3922 (1978).

F. Holmes et al., "Complex-forming Agents Similar to 2,2'-Bipyridyl. Part I. Some Ligands containing Imidazole.", *J. of the Chem. Soc.*, pp. 4790-4794 (1961).

D.W. Gruenwedel, "Multidentate Coordination Compounds. Chelating Properties of Aliphatic Amines Containing α-Pyridyl Residues and Other Aromatic Ring Systems as Donor Groups", *Inorganic Chemistry*, vol. 7, No. 3, pp. 495-501 (1968).

T. Leigh et al., "Synthesis of and Novel Reactions with Bis[imidazol-2-yl]nitromethane", *Synthesis*, pp. 459-461 (1977).

B.R. Green et al., "Poly(vinylimidazole)—a versatile matrix for the preparation of chelating resins", *Ion Exch. Technol.*, pp. 490-499 (1984).

H. Ritter et al., "Synthesis of 3',5'-bis(morpholinomethyl)-4'-hydroxy-and-3'5'-bis(4-methyl-1-piperazinylmethyl-4'-hydroxymethacrylanilide. Copolymerization and metal ion binding properties of monomers and copolymers", *Makromol. Chem.*, vol 187, pp. 801-807 (1986).

Y. Kurimura et al., "Complexation of Polymer-bound Imino Diacetate-type Chelating Agents with some Transition-metal Ions", *J. Chem. Soc., Faraday Trans. 1*, vol. 84, No. 3, pp. 841-850 (1988).

K. Volchek et al., "Selective Removal of Metal Ions from Ground Water by Polymeric Binding and Mirofiltration", *Desalination*, vol. 89, pp. 247-262 (1993).

G. Manecke et al., "Polymere Imidazolcarbonsäuren, 2", *Makromol. Chem.*, vol. 179, pp. 19-27 (1978).

Y. Onari, "Chelating Polymer Bearing 2-(2-Diazolylazo)phenol Moiety for Adsorbent of Heavy Metal Ions", *Analytical Sciences*, vol. 7, pp. 463-466 (1991).

F.M. Menger et al., "Lipid-Catalyzed Transport of Cu(II) through Liquid Membranes", *J. Org. Chem.*, vol. 58, pp. 1909-1916 (1993).

(List continued on next page.)

*Primary Examiner*—Joseph L. Schofer
*Assistant Examiner*—Wu C. Cheng
*Attorney, Agent, or Firm*—Scully, Scott, Murphy & Presser

[57] ABSTRACT

The present invention relates to bis-imidazolyl compounds of the formula:

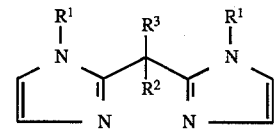

and polymers having the above-identified bis-imidazolyl compounds as a polymerizable unit. The present invention further relates to a method for scavenging trace quantities of metal ions from various effluents sources using the polymers of the instant invention. The instant invention also is directed to the use of the above-identified polymers as corrosion inhibiting agents and as a film for use in gel electrophoresis.

36 Claims, No Drawings

OTHER PUBLICATIONS

W.B. Tolman et al., "Self–Assembly and Dioxygen Reactivity of an Asymmetric, Triply Bridge Diiron(II) Complex with Imidazole Ligands and an Open Coordination Site", *J. Am. Chem. Soc.*, vol. 111, pp. 8522–8523 (1989).

D.F. Harvey et al., "Spin Frustration: A Hexanuclear Ferric Complex with a S=5 Ground State", *J. Am. Chem. Soc.*, vol. 113, pp. 6114–6124 (1991).

S.E. Boyd et al., "Synthesis and Structure of Diacetato-[1–benzyloxy–1,1–bis(N–methylimidazol–2–yl)ethane]zinc (II)", *Aust. J. Chem.*, vol. 46, pp. 1307–1312 (1993).

J.K. McCusker, C.A. Christmas, P.M. Hagen, R.K. Chadha, D.F. Harvey, D.N. Hendrickson, J. Am. Chem. Soc. 113, 6114–6124, 1991.

S.E. Boyd, M.M. Harding, I.E. Buys, T.W. Hambley, Aust. J. Chem. 46, 1307–1312, 1993.

S. Ohta, S. Hayakawa, H. Moriwaki, S. Harada, and M. Okamoto, Chem. Pharm. Bull. 34, 4916–4926, 1986.

METAL ION BINDING MONOMER AND POLYMER

CROSS-REFERENCE TO RELATED APPLICATIONS

This is divisional of application Ser. No. 08/317,433 now abandoned, filed on Oct. 3, 1994, which is a C-I-P appln. U.S. Ser. No. 08/130,330 now U.S. Pat. No. 5,455,359, filed on Oct. 1, 1993.

This present research project was partially supported by a grant from the Blandin Foundation.

FIELD OF THE INVENTION

The present invention relates to novel bis-imidazolyl compounds and to polymers which contain the novel bis-imidazolyl moieties therein as a polymerizable unit. The present invention further relates to the use of these polymers for water treatment, preservation of machine oils, films for gel electrophoresis, packing materials for columns and for protective coatings for various metal surfaces. The instant invention also relates to a kit which comprises a filter having the polymers of the present invention therein. The present invention also relates to the use of these polymers for recovery of precious metals from waste water streams and mines.

BACKGROUND OF THE INVENTION

Those skilled in the art are well aware of the technological importance of chelating agents for removing metal ions from various effluents, such as waste water, plating baths and the like. Chelating agents provide means of manipulating and controlling metal ions by forming complexes that usually have properties that are markedly different from those of the original metal ions or the chelators. These properties may serve to reduce undesirable effects of metal ions in drinking water, waste water, sewage and the like. Thus, new and improved chelating agents are continuously being developed which have a high selectivity and capacity for binding various metal ions.

An important class of chelating agents are those which are derived from a bis-imidazolyl moiety. These compounds have shown an excellent ability to bind various metal ions, especially $Cu^{2+}$, effectively due to the proximity of the lone electron pairs on each of the nitrogen atoms in the imidazolyl rings.

Extensive studies of various bis-imidazolyl compounds have been conducted in recent years to determine the binding characteristics of these compounds, See, for example Drey, et al. "Metal Chelates of Bis-Imidazole," *Biochemistry*, Vol. 4, No. 7, pp. 1258–1263, Jul. 1965 and Breslow, et al., "Models or Metal Binding Sites in Zinc Enzymes. Synthesis of Tris [4(s)-imidazolyl]carbinol (4-TIC), Tris (2-imidazolyl)carbinol (2-TIC), and Related Ligands, and Studies on Metal Complex Binding Constants and Spectrum," *JACS*, Vol. 100, No. 12, pp. 3918–3922, June 1978.

A specific bis-imidazolyl compound that has been developed in recent years is disclosed in U.S. Patent No. 4,869,838 to Gorun et al. More specifically, the reference discloses a bis-imidazole ether of the following formula:

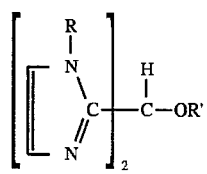

wherein R is a normal alkyl group having from 1 to 12 carbon atoms and R' is a normal alkyl group having from 7 to 12 carbon atoms, an alkylaryl group having from 7 to 20 carbon atoms, or an aryl group of 6 to 10 carbon atoms. The above-identified bis-imidazolyl ether compounds are useful for complexing metal ions which are present in lubricating oils.

Despite the current state of the art, there is still a need for developing new metal chelators that have the ability to selectively and reversible bind metal ions. Additionally, due to the growing awareness of the environment in recent years, there is a continual need for developing new metal chelators that have the capacity for binding large quantities of trace amounts of metal ions from various effluent streams.

SUMMARY OF THE INVENTION

The present invention is directed to novel compounds of the formula:

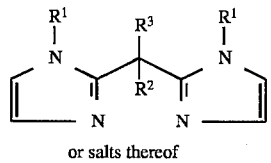

or salts thereof wherein $R^1$ is hydrogen, lower alkyl, lower alkenyl, lower alkynyl or lower alkoxy; $R^2$ is lower alkoxy or hydroxy or acroyloxy; and $R^3$ is lower alkyl, lower alkenyl, carboxylvinyl, lower carbalkoxyvinyl wherein the alkyl group thereof is unsubstituted or substituted with phenyl or $(CH_2)l$-OH or combination thereof; a substituted or unsubstituted aryl containing 6 to 10 ring carbon atoms wherein the substituents on the ring carbon atoms are independently hydrogen, lower alkyl, lower alkenyl, lower alkynyl, lower alkoxy, halogen, sulfato, nitro, lower alkanoyl or formyl;

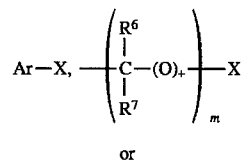

or

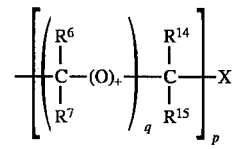

or $R^2$ and $R^3$ taken together form —=$CR^4R^5$- or oxo, wherein $R^4$ and $R^5$ are the same or different and are hydrogen, lower alkyl or carboxy or lower carbalkoxy;

$R^6$ and $R^7$ are independently hydrogen, lower alkyl, lower alkenyl, lower alkynyl, lower alkoxy, sulfato, lower alkanoyl, carboxy, lower carbalkoxy, or formyl or $R^6$ and $R^7$ taken together with the carbon atoms to which they are attached form

each $R^8$ and $R^9$ are independently hydrogen, lower alkyl, lower alkenyl, lower alknyl, carboxy, lower carbalkoxy, or

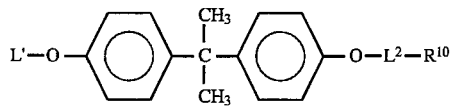

$L^1$ and $L^2$ are independently

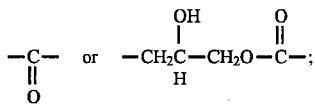

$R^{10}$ is

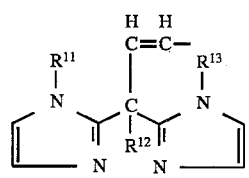

Ar is aryl, $R^{11}$ and $R^{13}$ are independently hydrogen, lower alkyl, lower alkenyl, lower alknyl or lower alkoxy;

$R^{12}$ is hydroxy, lower alkoxy or lower alkyl;

$R^{14}$ and $R^{15}$ are independently hydrogen, lower alkyl, lower alkenyl, lower alknyl, lower alkoxy, halogen, sulfato, nitro, lower alkanoyl, formyl, carboxy, lower carbalkoxy or $R^{14}$ and $R^{15}$ taken together with the carbon atom to which they are attached form

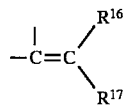

$R^{16}$ and $R^{17}$ are independently hydrogen, lower alkyl, lower carbalkoxy, carboxy or

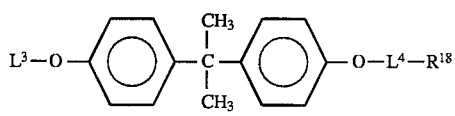

$L^3$ and $L^4$ are independently

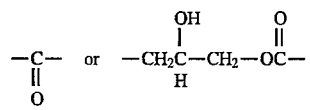

$R^{18}$ is

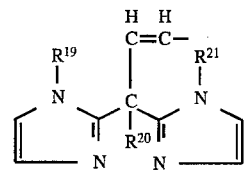

$R^{19}$ and $R^{21}$ are independently hydrogen, lower alkyl, lower alkenyl, lower alkenyl, or lower alkoxy;

$R^{20}$ is hydroxy, lower alkoxy or lower alkyl;

X is hydrogen, lower alkyl, lower alkenyl, lower alknyl, lower alkoxy, halogen, sulfato, nitro, lower alkanoyl, formyl, carboxy, lower carbalkoxy,

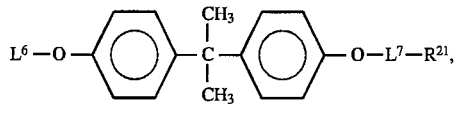

or

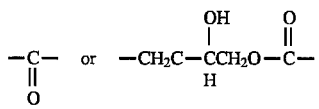

$L^6$ and $L^7$ are independently

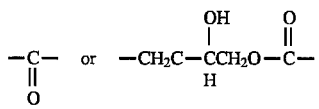

$R^{21}$ is

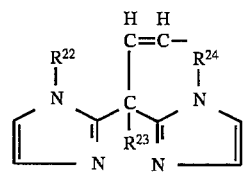

$R^{22}$, $R^{24}$, $R^{25}$ and $R^{27}$ are independently hydrogen, lower alkyl, lower alkenyl, lower alkynyl or lower alkoxy;

$R^{23}$ and $R^{26}$ are independently hydroxy, lower alkoxy or lower alkyl.

m=0–15, and preferably 1–15 q=0 or 1 p=0–15, and preferably 1–15 t=0 or 1 and
l=0–5.

The present invention also relates to polymers which comprise the polymerizable unit of the following formula:

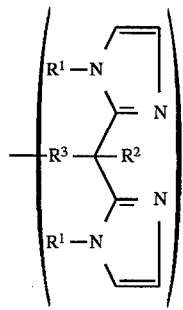

II wherein $R^1$ is hydrogen, lower alkyl, lower alkenyl, lower alkynyl or lower alkoxy; $R^2$ is lower alkoxy or hydroxy; $R^3$ is lower alkylene, $MOOC-CH_2-CH_2-$ or a substituted arylene containing 6 to 10 ring carbon atoms 15 wherein the substituents on the ring carbon atoms are independently hydrogen, lower alkyl, lower alkenyl, lower alkynyl, lower alkoxy, halogen, sulfate, nitro, lower alkanoyl or formyl, and M is H or a cation.

The foregoing polymerizable unit may also be combined with other polymerizable units to form novel copolymers, block copolymers, latex polymers, thermoplastic polymers, and the like.

The polymers formed from these monomers may be attached to polyethylene or cellulose for use as filters.

Also, the present invention relates to a method for removing trace quantities of heavy metal ions from various waste water effluents using the aforementioned polymers and to a kit that contains a filter having the novel bis-imidazolyl polymers therein.

The present invention is further directed to the use of the novel polymers as a corrosion inhibiting agent, a column packing material and a film for use in gel electrophoresis or a catalyst for curing of epoxy, especially dry powder epoxy, coatings or resins.

DETAILED DESCRIPTION OF THE INVENTION

As described hereinabove, the present invention encompasses compounds of the formula:

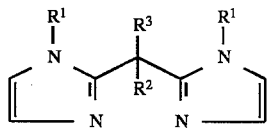

I wherein $R^1$, $R^2$ and $R^3$ are as defined hereinabove.

These compounds can be divided into two classes of compounds. In one class, the monomers are non-polymerizable, while in another class, the monomers are polymerizable. Compounds of the present invention which are polymerizable contain multiple bonds, e.g., double bonds or triple bonds, with double bonds being more preferable. The monomers may contain more than one double bond. The double bond(s) may be in conjugation with an aryl group, such as a phenyl group or with an carbonyl group, such as acroyl. When the monomer polymerizes, the double bond becomes saturated. For example, assuming for purposes of discussion A is a bis-imidazoyl moiety with the following structure:

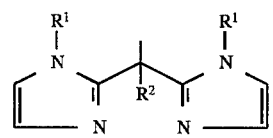

then if the monomer has a double bond, such as $$A-\underset{H}{C}=\underset{H}{C}-CO_2H,$$

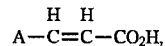

then a polymer resulting therefrom would have the following repeating unit:

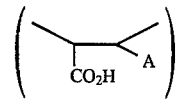

As used herein, the alkyl groups, when used alone or in combination with other groups are lower alkyls containing from 1 to 6 carbon atoms and may be straight chained or branched. These groups include methyl, ethyl, propyl, isopropyl, butyl, isobutyl, tertiary butyl, pentyl, hexyl, and the like.

As used herein, the term "lower alkoxy" refers to —O—alkyl groups, wherein the alkyl is defined hereinabove. The alkoxy group may be straight chained or branched; although the straight-chain is preferred. Examples include methoxy, ethoxy, propoxy, butoxy, t-butoxy, i-butoxy, i-propoxy, and the like.

The term lower alkenyl is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g. 1,3 or 2,4-pentadienyl, and the like.

The term alkynyl includes alkynyl substituents containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl, and the like.

The term lower alkanoyl as used herein means an alkyl group containing 1 to 6 carbon atoms which contains an oxo substituent therein. Preferred alkanoyls are those wherein the —C=O— group is attached directly to the aryl group. Such groups include ethanoyl, propanoyl, butanoyl, and the like.

The term halogen includes fluoro, chloro, bromo, iodo and the like.

The term aryl, when used alone or in combination, refers to an aromatic group which contains from 6 up to 10 ring carbon atoms. The aryl groups are monocyclic or bicyclic groups that may be substituted or unsubstituted. If substituted, the substituents on the ring carbon atoms may be independently hydrogen, lower alkyl, lower alkenyl, lower alkynyl, lower alkoxy, halogen, sulfate, nitro, lower alkanoyl or formyl. The aryl groups include phenyl, α or β naphthyl, and the like. The aryl group may be mono, di or tri-substituted. It is preferred that the aryl group is at least monosubstituted.

The term "acroyl" refers to a group of the formula

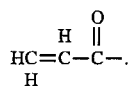

In addition, "carboxyvinyl" refers to the group of the

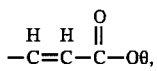

i.e., it refers to the basic form of the acrylic acid (acrylate) wherein the carboxylate is attached to the main chain through a

bridging group. The acrylate is part of a salt which is solvated in aqueous solution and wherein the cationic portion thereof is either a $H^+$, ammonium or a metal cation, such as an alkali or alkaline earth metal of the periodic table. Moreover, the term "carbalkoxyvinyl" refers to the lower alkyl ester of the acrylic acid moiety, i.e.

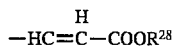

wherein $R^{28}$ is lower alkyl.

On the other hand, acroyloxy refers to the moiety

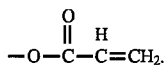

The term "salts" refers to an ionic compound containing a cationic portion and an anionic portion. If the anionic portion is inorganic, such as acrylate, the cationic portion is ammonium, hydrogen or any suitable metal cation which are known to one skilled in the art. The preferred cations are ammonium and the metal cations from Groups IIIA, and expecially Groups IIA and IA from the periodic table. Hydrogen, ammonium, and the Group IA metals, such as sodium, lithium, potassium, and the like are the most preferred.

If the cationic portion is organic, such as protonated imidazole then the anionic portion are inorganic or organic radicals that are typically used in this art. Examples include acetate, oxalate, sulfate, sulfite, phosphates, phosphite, chromate, permanganate, formate, carboxylate, halate, halide, hydroxide, oxide hypohalite and the like.

The term "cation" refers to a cation referred to hereinabove, i.e., $H^+$, $NH_4^+$, or metal cation, especially Group IA and IIA metals.

The preferred values of $R^1$ are hydrogen, vinyl and especially lower alkyl containing from 1 to 3 carbon atoms. The most preferred value of $R^1$ is methyl.

The preferred values of $R^2$ are hydroxy or methoxy, acroyloxy, with hydroxy being especially preferred.

Preferred values of $R^3$ are a lower alkyl or a substituted or unsubstituted aryl. When $R^3$ is lower alkyl it is preferred that the lower alkyl group contains from 1 to 3 carbon atoms. The most preferred lower alkyl is methyl. When $R^3$ is a substituted aryl it is preferred that the substituted aryl be phenyl. It is especially preferred that $R^3$ be styryl.

Other preferred values of $R^3$ include the moieties:

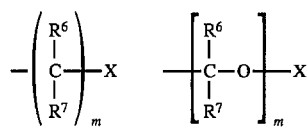

Preferred values of $R^6$ and $R^7$ are hydrogen, lower alkyl, which is unsubstituted or substituted with carboxy or salts thereof or carbalkoxy. The preferred lower alkyl is methyl and especially ethyl. It is also preferred that the lower alkyl substituent is 2-carboxyethyl or 2-(carbalkoxy)ethyl, or the carboxylate salt thereof.

It is also preferred that $R^6$ and $R^7$ taken together with the carbon to which they are attached form

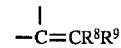

Preferred values of $R^8$ and $R^9$ are independently hydrogen, lower alkyl or

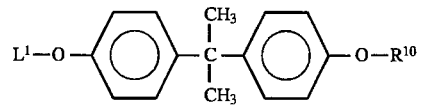

wherein $L^1$ and $L^2$ are as defined hereinabove. When $L^1$ and $L^2$

then the group formed thereby, the

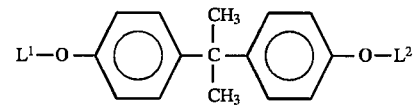

is preferred to as the carboxylate ester of Bisphenol A. On the other hand, when $L^1$ and $L^2$ are

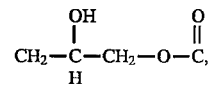

then, the group formed thereby, the

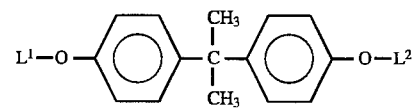

is referred to as the carboxylate ester of a glycidyl ether of Bisphenol A.

Preferred values of $R^{10}$ are

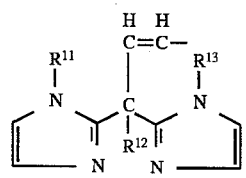

wherein $R^{11}$ and $R^{13}$ are the same and are preferably alkyl. It is especially preferred that $R^{11}$, $R^{13}$ and $R^1$ have the same meaning, and even more preferred that $R^{13}$, $R^{11}$ and $R^1$ be the same alkyl group. It is most preferred that $R^{12}$, $R^{11}$ and $R^1$ be methyl. Preferred values of $R^{12}$ are alkoxy and especially hydroxy.

The values of X that are preferred are hydrogen, lower alkyl, and

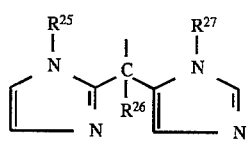

It is preferred that $R^{25}$ and $R^{27}$ are the same. It is even more preferred that $R^{25}$ and $R^{27}$ both be alkyl, especially methyl. It is especially preferred that $R^{25}$, $R^{27}$, $R^{11}$, $R^{13}$ and $R^1$ are all the same. It is more especially preferred that $R^{25}$, $R^{27}$, $R^{11}$, $R^{13}$ and $R^1$ be the same alkyl group. It is most especially preferred that $R^{25}$, $R^{27}$, $R^{11}$, $R^{13}$ and $R^1$ are all methyl.

The most preferred values of $R^{14}$ and $R^{15}$ are independently hydrogen, lower alkyl, lower alkenyl. Other preferred values of $R^{14}$ and $R^{15}$ are when they are taken together with the carbon atom to which they are attached to form

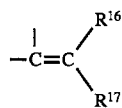

Preferred values of $R^{16}$ and $R^{17}$ are hydrogen, lower alkyl or

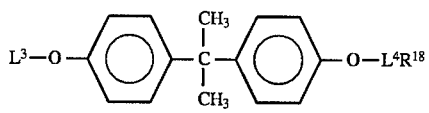

Preferred values of $R^{18}$ are the same as $R^{10}$. Thus, it is preferred that $R^{19}$ and $R^{21}$ be the same as $R^{11}$ and $R^{13}$, respectively and that $R^{19}=R^{21}=R^{11}=R^{13}$. It is even more preferred that $R^{11}=R^{13}=R^{19}=R^{21}$ alkyl, especially methyl.

The preferred value of $R^\circ$ is lower alkoxy and especially hydroxy.

When $R^2$ and $R^3$ form $=CR^4R^5-$, this means that the carbon atom that bridges the two imidazole moieties in Formula I forms a double bond; so that the compound of formula I becomes

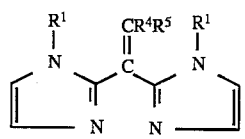

In this formulation, it is preferred that at least one of $R^4$ and $R^5$ is methyl. It is also preferred that one of $R^4$ and $R^5$ is hydrogen. It is most preferred that both $R^4$ and $R^5$ be methyl. It is also preferred that one of $R^4$ and $R^5$ is lower carbalkoxy or carboxy or a salt thereof.

When $R^2$ and $R^3$ form an oxo, this means that the compound of formula I becomes

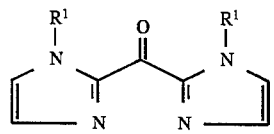

In this formulation, it is preferred that $R^1$ is lower alkyl, and especially alkenyl. It is also preferred that both $R^1$ are the same. The most preferred value of $R^1$ is lower alkenyl, especially vinyl.

In the formula hereinabove, the term "$R^6$ and $R^7$ taken together with the carbon atom to which they are attached form $-CR^8R^9-$" refers to the following moieties in the definition of $R^3$:

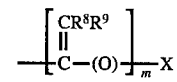

or

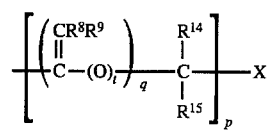

Similarly, in the definition of $R^3$, the term $R^{14}$ and $R^{15}$ taken together with the carbon atom to which they are attached form

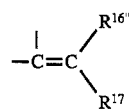

refers to the following moiety:

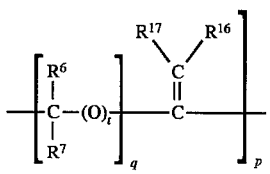

A preferred class of bis-imidazolyl compounds are represented by the following formula:

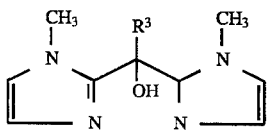

wherein $R^3$ is a lower alkyl,

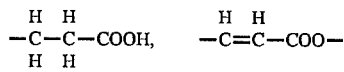

or a substituted aryl compound. When $R^3$ is lower alkyl, it is preferred that the lower alkyl contains from 1 to 3 carbon atoms. The most preferred lower alkyl is methyl. When $R^3$ is a substituted aryl it is preferred that the substituted aryl be phenyl and that it be monosubstituted. It is especially preferred that $R^3$ be styryl.

Another preferred class of bis-imidazolyl compounds are those that are represented by the following formula:

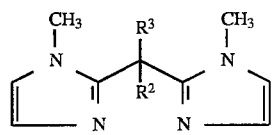

wherein $R^2$ and $R^3$ taken together form $=CR^4R^5-$ wherein $R^4$ and $R^5$ are the same or different and are lower alkyl, hydrogen or carboxy. It is preferred that one of $R^4$ and $R^5$ is hydrogen or lower alkyl, especially methyl and the other is hydrogen, lower alkyl, especially methyl or carboxy, especially a salt thereof.

The most preferred bis-imidazolyl compounds encompassed by Formula I are those wherein:

$R^1$ is methyl, $R^2$ hydroxy and $R^3$ is methyl;

$R^1$ is methyl, $R^2$ hydroxy and $R^3$ is styryl;

$R^1$ is methyl, $R^2$ methoxy and $R^3$ is styryl;

$R^1$ is methyl, $R^2$ hydroxy and $R^3$ is acrylate (e.g., sodium acrylate).

Other preferred bis-imidazolyl compounds encompassed by Formula I are $$A-\underset{H}{C}=\underset{H}{C}-COOH,\ A-(CH_2)_m-A,\ A-(CH_2-O)_{\overline{m}}A,\ H-(CH_2)_m-A,\ A-\overset{O}{\underset{\|}{C}}-A$$

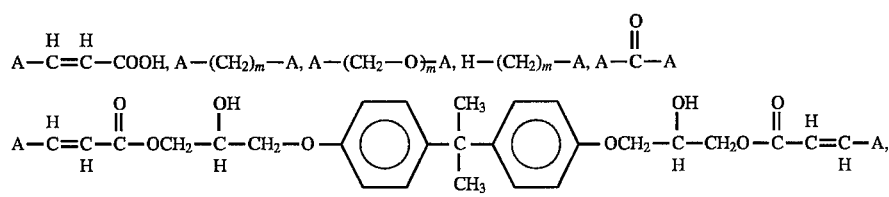

or

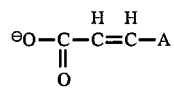

wherein

A is

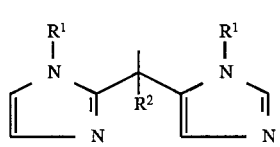

$R^1$ is methyl or vinyl, $R^2$ is OH or acroyloxy, and

M is a cation, preferably $H^+$, alkali or alkaline earth methyl or ammonium.

Specific examples include:

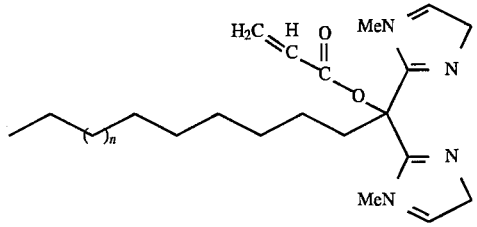

wherein n is 1–20, and especially 3.

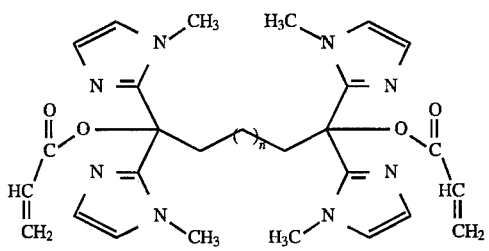

wherein n is 1–20, and preferably 6.

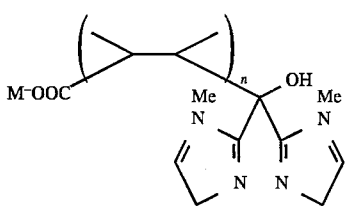

wherein n is 1–4,000 and preferably 100–1,000.

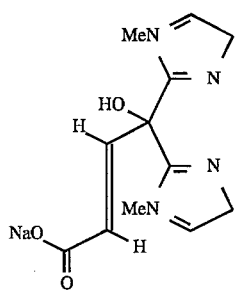
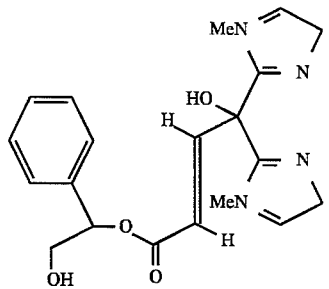
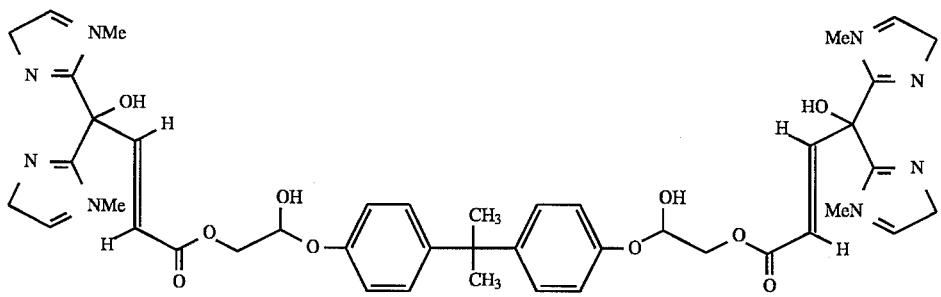
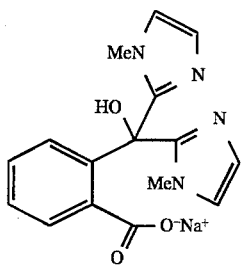
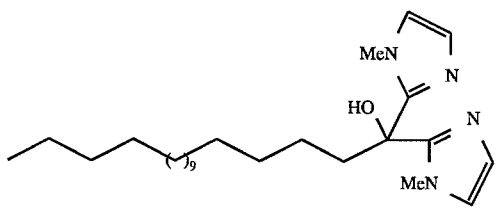
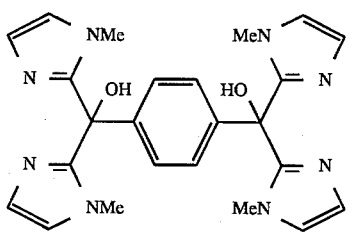

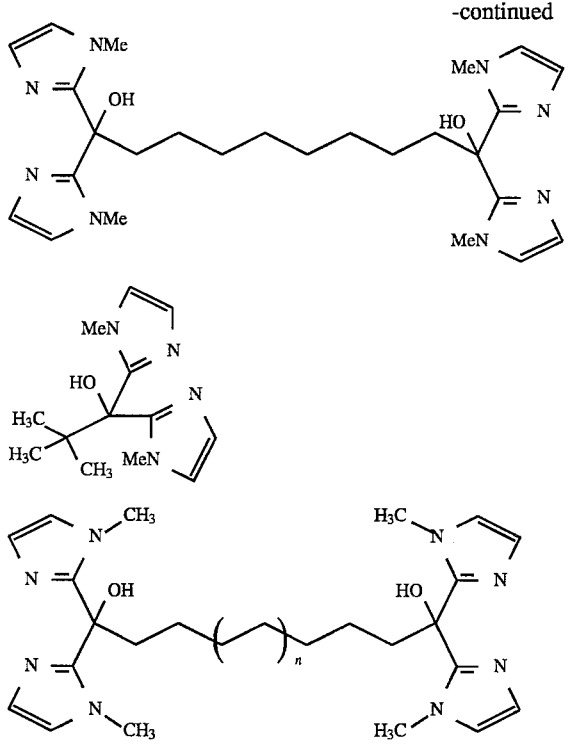

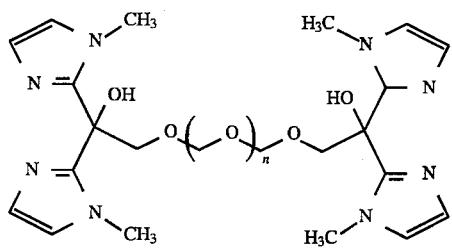

wherein n is 0–2, and preferably n is 0.5.

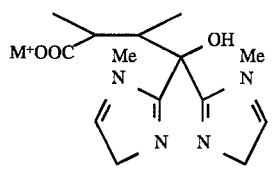

wherein n is 1–10;

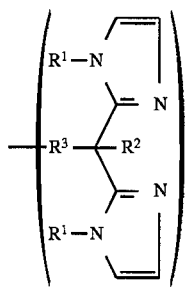

The present invention further relates to polymers which comprise the polymerizable unit of the following formula II:

wherein the variables $R^1$ and $R^2$ have the above-identified meaning and $R^3$ is lower alkylene, $$-\underset{H}{\overset{H}{C}}-\underset{H}{\overset{H}{C}}-COOH$$

or a substituted arylene containing from 6 to 10 ring carbon atoms wherein the substituents on the ring carbon atoms are independently hydrogen, lower alkyl, lower alkanoyl, lower alkenyl, lower alkoxy, halogen, sulfate, nitro, or formyl. As used herein, the arylene group is an aryl group which is substituted to the polymeric chain in two positions, i.e. —Ar—. It is preferred that the arylene group is monosubstituted, but the arylene may be mono-, di- or tri-substituted. As used herein the term "styrylene" refers to the phenylethylene unit.

Unless indicated to the contrary, the term polymerizable "unit" refers to the above structural moiety of Formula II.

Homopolymers of the present invention are compounds of the formula

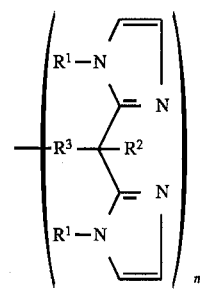

wherein $R_1$, $R_2$ and $R_3$ are as defined hereinabove and n is an integer from 2 to 100,000. Preferred values of n are between about 50 to about 1000. The most preferred values of n range from about 100 to about 500.

The preferred values of $R^3$ in the polymerizable unit are

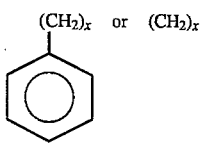

wherein
x is an integer from 2 to 6. Especially preferred values of x are from 2 to 4.

Another preferred value of $R_3$ in the polymerizable unit is $CH_3$—$CH_2$—COOH or salt thereof ($CH_2CH_2COO^-M^+$, wherein $M^+$ is a cation, e.g. $NH_4^+$, $H^+$, metal cation, such as alkali metal, alkaline earth metal, and so on).

It should be noted that the polymers of the present invention may be homopolymers as described hereinabove containing only repeating bis-imidazolyl monomeric units. Alternatively, they can be copolymers, block copolymers, latex polymers, thermoplastic polymers, and the like. That is, the polymerizable units of the present invention described hereinabove may be polymerized with other polymerizable monomers that are presently available to form copolymers, block copolymers, latex polymers and thermoplastic. Suitable polymerizable monomers that can be polymerized with the identified polymerizable units of Formula II include those wherein $R^3$ is lower alkene units or arylalkene units, such as ethylene, propylene, 1-butylene, styrene, acrylates and the like and $R^1$ and $R^2$ are as defined hereinabove. Examples include polystyrene-, polyethylene- and polyacrylate bis-imidazole moieties. Examples include bis- methylimidazole functionalized styrene/maleic anhydride copolymer, bis-methylimidazole functionalized ethylene/maleic anhydride copolymer and the like. The ratios of the copolymers range from 0:100 to 100:0 (w/w). For example, when the copolymers are bis-methyl imidazole functionalized styrene/maleic anhydride, the ratios range from 80:20 to 0:100 (w/w) respectively. A preferred bismethylimidazole functionalized ethylene/maleic anhydride copolymer is in a 1:1 ratio (w/w).

In addition, the polymers of the present invention or the copolymers of the present invention may be crosslinked with crosslinkers, such as divinylbenzene. In an embodiment of the present invention, the polymer or copolymer of the present invention is cross-linked with divinylbenzene, preferably divinylbenzene is present in amounts less than 2% (w/w) and more preferably in amounts ranging from 1–2% divinylbenzene (w/w).

The preferred values of $R^1$ and $R^2$ for the polymerizable units of the present invention are the same as those mentioned hereinabove regarding the bis-imidazolyl compounds. For example, the preferred values of $R^1$ are hydrogen or lower alkyl containing from 1 to 3 carbon atoms. The most preferred value of $R^1$ is methyl. The preferred values of $R^2$ are hydroxy or methoxy, with hydroxy being especially preferred.

The preferred values of $R^3$ of the polymerizable units of the present invention are those that are indicated hereinabove. For example, a preferred value of $R^3$ is wherein $R^3$ is a substituted arylene. Another preferred value of $R^3$ is when $R^3$ is lower alkylene. In this embodiment, it is preferred that the lower alkylene contains from 1 to 3 carbon atoms. The most preferred lower alkylene is methylene. Another preferred value of $R^3$ is, as indicated hereinabove, $CH_2CH_2COOM$. When $R^3$ is a substituted arylene, it is preferred that the arylene be a mono- or disubstituted phenylene. It is especially preferred that $R^3$ be styrylene. The most preferred polymers of the present invention are those wherein the polymers have the following formula:

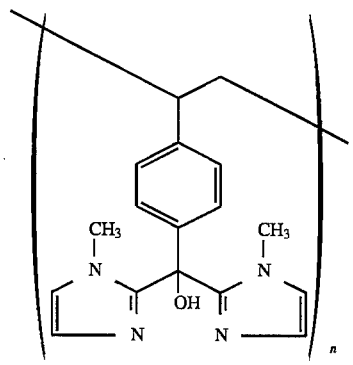

wherein n is an integer ranging from about 2 to about 100,000. Preferred values of n are between about 50 to about 1000. The most preferred values of n range from about 100 to about 500. This particular embodiment is directed to polymers that contain repeating units of a bis-methylimidazolyl styrenyl compound. That is, the formula shown hereinabove relates to homopolymers containing only the bis-methylimidazolyl styrenyl monomeric unit.

Another preferred polymer of the present invention is represented by the following formula:

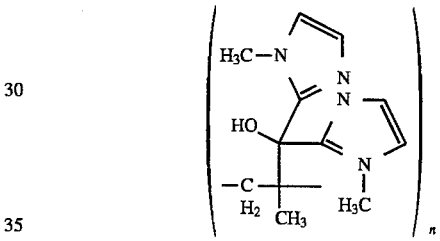

wherein n is an integer ranging from about 2 to about 100,000, and M is as defined hereinabove. Especially preferred values of n are from 500 to about 2000. Most preferably, n is from about 1000 to about 1500. The above formula represents a poly(bis-methylimidazolyl) polymer.

A preferred polymer of the present invention has the formula:

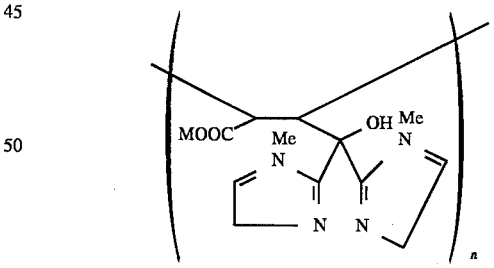

wherein n is an integer ranging from about 2 to about 100,000 and M is as defined hereinabove. Especially preferred values of n range from 50 to about 1,000. The most preferred values of n range from about 100 to about 500.

The following scheme of preparation is generally exemplary of the process which can be employed in the preparation of bis-imidazolyl compounds of Formula I of the instant invention. Although the compounds in the reaction scheme are specific for values of $R^1$ being methyl, $R^2$ being hydroxy and $R^3$ being styryl, it is just as applicable to compounds that have different values of $R^1$, $R^2$ and $R^3$ as defined hereinabove.

SCHEME I

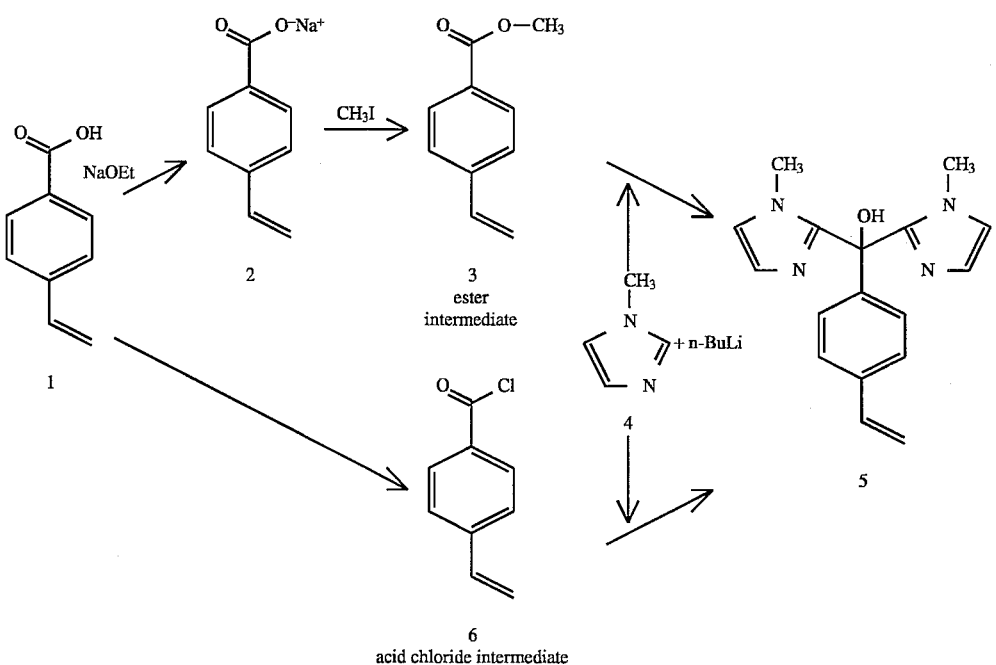

3 ester intermediate 6 acid chloride intermediate

Scheme I outlines a general methodology for reacting an acylating intermediate, such as an ester or acid chloride, with an imidazole anion to form the product of Formula I. However, Scheme I shows two alternative methods for preparing bis-imidazolyl compounds of the present invention.

In one method, as shown in the top portion of this reaction scheme, 4-vinylbenzoic acid (1) is esterified by techniques known to one skilled in the art. For instance, compound 1 is reacted with a base, e.g. sodium ethoxide, in an organic solvent which is non-reactive with the reagents and in which 1 and the reactants are soluble, such as dimethyl formamide (DMF). This particular reaction step serves to remove a hydrogen from compound 1 to create a sodium salt, 2. This sodium salt compound is then combined with iodomethane ($CH_3I$) in DMF solvent under heat and a nitrogen atmosphere to form the ester intermediate, 3. An imidazole anion e.g., methylimidazole anion, 4, is then prepared by dissolving a suitable quantity of the imidazole in a suitable solvent, e.g. tetrahydrofuran (THF), at low temperatures, e.g. $-78°$ C., in a dry ice/ethanol. bath. A strong base capable of removing a hydrogen from the imidazole, such as n-butyllithium (n-BuLi), is reacted with the imidazole at cold temperatures, e.g. $-78°$ C. or lower, and this product is then reacted with the acylating intermediate to form the product of Scheme I (5).

In the alternative route of this reaction scheme which is illustrated in the lower portion of Scheme I, vinylbenzoic acid 1 is reacted with thionyl chloride ($SOCl_2$) to create the acid chloride intermediate, 6. The acid chloride intermediate thus formed is then added to a solution of 4 and n-BuLi in the same manner as mentioned hereinabove.

It should be noted that the process illustrated in the lower half of this reaction scheme is the preferred method of making the bis-imidazolyl compounds of the present invention since it involves one less reaction step and that acid chloride intermediates produced by this route are generally more reactive than their ester counterparts.

As shown by the scheme hereinabove, there are 2-imidazoyl moieties that are utilized for every acylating group.

The above scheme is generalized as follows:

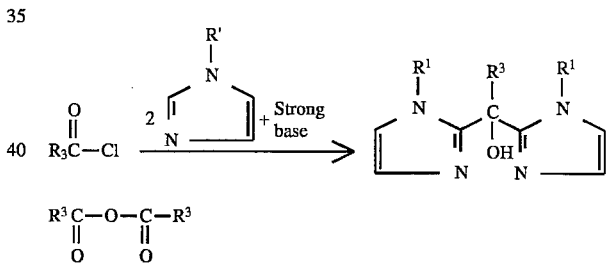

In other words, an acylating derivative of

such as the acid chloride,

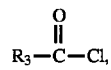

is reacted with an imidazole anion followed by protonation to form the alcohol containing product. The imidazole anion is generated by reacting the imidazole with a strong base, for instance, a metal alkylide (e.g. alkali alkylide, such as n-BuLi).

Although the reaction above is illustrated for an acid chloride, the synthetic scheme works with any acylating derivatives of

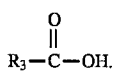

An anhydride may be utilized, for example,

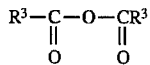

wherein $R_3$ is as defined hereinabove. Please note that although the $R^3$'s of the above anhydride may be the same or different it is preferred that both $R^3$s are the same.

The anhydride does not necessarily have to be linear; it can be cyclic. For instance, a method for preparing the acrylate moiety for $R^3$ is by reacting a maleic anhydride with the imidazole anion. An exemplary procedure wherein $R^1$ is methyl and the anhydride or maleic anhydride is shown below, but the scheme is general and is applicable for the preparation of compounds wherein $R^1$, $R^2$ and $R^3$ are as defined herein:

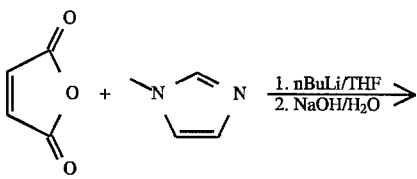

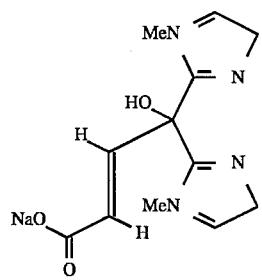

The reaction is conducted in a suitable solvent that is inert to both the reactants and products and in which the reactants are soluble. Examples of suitable solvents include THF, DMF, and the like. If the metal salt is desired, then the work-up includes the step of reacting the product with a base, such as metal hydroxide in $H_2$ or other basic salt soluble in $H_2$. If $NH_4^+$ is the cation, then $NH_4^+$ OH may be utilized as the base. If the acid form is desired, then the product is worked up in acids, such as HCl or $H_2SO_4$.

Although a compound of the present invention containing the hydroxy substituent shown hereinbelow

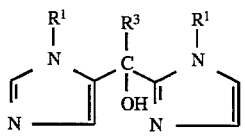

is useful as described hereinbelow, this compound is also an intermediate for making other compounds of the present invention which are also useful. For example, to generate an alkoxy group at $R^2$, the above compound is reacted under Williamson reaction conditions with an alkyl halide. For instance, the alkoxide of the above formula generated by, for example, reacting the above compound with base, such as hydroxide, is reacted with an alkyl halide under Williamson reaction conditions to generate the alkoxy substituent for $R^2$.

If $R^2$ is an ester, then the above formula is reacted under esterifying conditions with an acylating derivative of

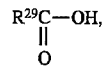

such as the acid halide (chloride, bromide, etc), acid in the presence of an acid catalyst, and the like to generate the ester. In this formula,

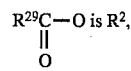

wherein $R^{29}$ is lower alkyl, lower alkenyl, and the like.

Polymerization of the polymerizable unit is done under polymerization conditions, e.g., free radical generation. Effective amounts of free radical initiators effective to form free radical intermediates are utilized. These may be commercially available or prepared in situ. For example, organic peroxides, such as bi(lower)alkanoyl peroxides, aryloyl lower alkanoyl peroxides, biarylyl alkanoyl, e.g., benzoyl peroxide, AIBN or the like may be employed by the present invention. Alternatively, UV light may be used to generate free radicals. In fact, UV light and organic peroxide may be used in combination.

Different approaches can be taken in synthesizing the bis-imidazolyl polymers of the present invention and these various techniques are known to one skilled in the art. For instance, a bis-imidazolyl compound of Formula I is dissolved in a suitable polymerizable compound in appropriate weight percent ratios and then polymerized. Suitable polymerizable compounds include lower alkene, or arylalkene, e.g., ethylene, propylene, 1-butylene, styrene/ divinylbenzene, lower alkylene oxy carbonyl-lower alkene, lower alkylene oxy carbonyl lower arylalkene, such as ethylene glycol dimethacrylate (EGDMA), lower alkanols, such as methanol, and the like. These polymerizable compounds are used in the present invention as backbones to which the functionalized imidazolyl compounds are directly bound to. The weight % ratio of the bis-imidazolyl compound to polymerizable compounds may vary over a wide range depending on the type of polymer being produced.

Typically, the weight % ratio of bis-imidazolyl compound to these polymerizable compounds varies from about 1 to about 100. Preferably, this weight % ratio of bis-imidazolyl compound to these polymerizable compound is from about 10 to about 90. The most preferred weight % ratio is from 40 to about 80.

Polymerization of the dissolved solution is performed by art-recognized techniques. For example, polymerization is initiated by adding an organic peroxide, such as benzoyl peroxide, or azodiisobupyronitrile (AIBN) derivative and then heating or exposing the solution to Ultraviolet light.

The amount of the organic peroxide compound or AIBN derivative that is employed in the present invention is from about 0.5 to about 10 weight %. More preferably, the amount of organic peroxide compound or AIBN derivative that is needed to initiate the polymerization is from about 0.5 to about 2 weight %.

Another process for preparing the polymers of the present invention is shown in reaction Scheme II.

SCHEME II

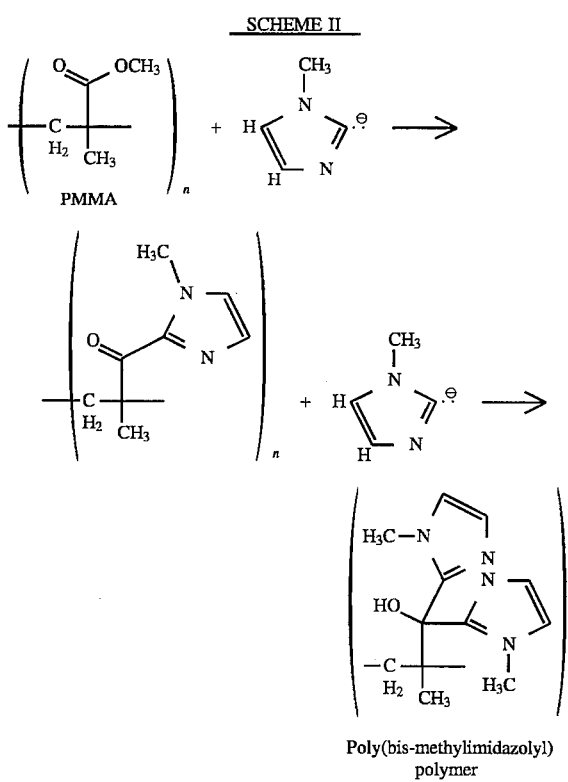

Poly(bis-methylimidazolyl) polymer

Two imidazole anions, generated as described hereinabove, react with a polymerizable compound, such as PMMA, to generate the product. Without wishing to be bound, it is believed that a methylimidazolyl anion, which is generated in-situ by reacting 1-methylimidazole with n-BuLi, undergoes a nucleophilic substitution reaction with the ester moiety of poly(methylmethacrylate) (PMMA) to form a ketone intermediate. This intermediate is then subsequently attacked by another methylimidazolyl anion to form a bis-methyimidazolyl alkoxy anion (this particularly species is not shown in the foregoing reaction scheme). This species is then quenched with a suitable quenching agent, such as water, to form the poly(bis-methylimidazolyl) polymer.

The present invention is further directed to a method for scavenging or removing heavy metal ions from various effluents that contain these ions. The term heavy metal ions as used herein connotates any metal that is heavier than calcium. The heavy metal ions also include such metals as aluminum and the lanthanide and actinide elements. It is most preferred that the metal ions be iron, copper, lead, mercury, cobalt, plutonium, thorium, zinc, and the like. Especially preferred metal ions include $Fe^{2+}$, $Cu^{2+}$, $Pb^{2+}$, $Hg^{2+}$, $Co^{2+}$, $Zn^{2+}$, $Fe^{3+}$, $Pu^{4+}$ and $Th^{3+}$. The most especially preferred metals include $Cu^{2+}$ and $Pb^{2+}$. The polymers of the present invention have a high affinity for chelating heavy metals, as defined herein, especially $Cu^{2+}$ and $Pb^{2+}$. By high affinity, it is meant that the polymers are able to remove very small amounts, in the ppb levels, of these ions from the effluent.

The polymers of the instant invention also exhibit a high capacity for binding heavy metals, such as $Cu^{2+}$ and $Pb^{2+}$ ions, even when these ions are present at extremely low concentration levels in a sample. For example, in the case of $Cu^{2+}$, the polymers of the instant invention exhibit a capacity which is greater than 5 meq/g. In another example, the polymers of the instant invention have a capacity for binding $Pb^{2+}$ that is greater than 3.9 meq/g. This represents an improvement over commercially available polymers or ion exchange resins that are currently employed in the art for removing heavy metal ions from waste water streams. Typically, the commercially available polymers provide chelating capacities near 1–2 meq/g for $Cu^{2+}$ and 0.5 meq/g for $Pb^{2+}$.

The specific method of the present invention for removing heavy metal ions from effluent streams involves first packing a column with a polymer having a polymerizable unit as defined hereinabove in Formula II. The column may be packed by conventional methods that are well known in the art. For instance, a suitable inert material, such as glass wool, is placed in the bottom of the column and then the polymer is poured into the column to form a resin bed. It is especially preferred that the polymers be made into resins or be finely crushed before it is poured into the column. Alternatively, the polymers can be processed into beads, fibers or films. These processes are well known in the art. After packing the column with the polymer, an inert material, such as sand or glass wool, is then placed on the top of the resin bed.

A portion of a waste water effluent is then added to the top of the polymer packed column and the sample is then allowed to elute through the polymer bed. Thereafter, the effluent is then collected at the bottom of the column in a suitable container.

The eluted sample is then analyzed for heavy metal ions, such as $Cu^{2+}$ and $Pb^{2+}$, using well known techniques in the art. For example, the samples may be analyzed by using Chemiluminescence, Gas Chromatography (GC), High Performance Liquid Chromatograph (HPLC), Atomic Absorption, Voltammetry, and the like. In the present invention Voltammetry is the preferred mode for analyzing the samples.

As mentioned hereinabove, the polymers of the present invention exhibit a high affinity as well as a high capacity for removing heavy metal ions. The capacity of the polymers of the present invention for binding heavy metal ions is higher than those previously reported using prior art polymer resins.

The present invention also provides a kit for removing heavy metals from various effluents, as described hereinabove. These metals can be present in the effluent at various concentrations including trace amounts, i.e., even as lower ppb levels. More specifically, the kit of the present invention comprises a filter which contains the novel polymers having the above-identified polymerizable unit therein. More specifically, the filter of the present invention comprises a disposable cartridge which contains the polymers of the present invention. The disposable cartridge employed by the filter of the instant invention could be in the form of a pleated cylinder, flat disc, hollow disc, and the like depending on the specific use of the filter. For example, if the filter is being used for purifying drinking water, the cartridge containing the polymer would typically be in the form of a pleated cylinder having pore sizes ranging from 0.01 to about 50 μm.

In another embodiment, the polymers of the present invention may be also used as a packing material for columns that are used in various analytic instruments, such as HPLC, GC, GC-MS, GLC, and the like. Columns comprising the polymers of the present invention would be especially useful for detecting heavy metal ions as defined herein, since the polymers exhibit a high affinity for such metal ions. Moreover, columns packed with the polymers of the present invention would be able to detect very low levels, i.e., ppb range, of these ions in a sample.

In this embodiment, the polymers would be finely grounded, processed into beads, fibers or films using techniques known to one skilled in the art and mixed with other commercially available packing materials such as silicon, alumina, and the like. The column would then be packed using common techniques that are well known and described in the art.

The polymers of the present invention may also be used as a film for gel electrophoresis. In this particular embodiment, the polymers are made into a thin film which may be used in gel electrophoresis for separating compounds that contain metal ions therein. Furthermore, the polymeric films of the present invention may also be mixed with commonly employed electrophoresis gels, such as starch gel, agar gel or polyacrylamide gel. By this technique, metal containing compounds can be separated from non-metal containing compounds, e.g. proteins can be separated from non-metal containing compounds. In addition, using the polymers of the present invention, various metal containing compounds can be separated from each other. Thus, for example, different proteins can be separated from each other by electrophoresis in which the electrophoresis gel is comprised of polymers of the present invention The polymer films for use in gel electrophoresis may be prepared by techniques well known in the art for making such a gel. For example, a finely ground or crushed form, or beaded form, or fiber, of the polymer can be made into a film by exposing it to heat or by treating it with a suitable solvent which would effectively dissolve the polymer. In the liquid state, the polymer could then be placed between two glass plates and then cooled to form a film for electrophoresis.

Alternately, the bis-imidazolyl compounds of the present invention may also be incorporated into a gel. In this embodiment, a bis-imidazolyl compound according to Formula I is polymerized with acrylamide to form a polymer which can be used in gel electrophoresis.

Compounds of the present invention, including monomers and polymers, are also useful as catalysts for curing epoxy, including dry powder epoxy, coatings or resins. For example, they can be incorporated into epoxy containing products, such as paints, lacquers, and anti-fouling agents, and the like, for purposes of protecting wood, metals, and other surfaces such as wall, floors and ceilings. These compounds are especially useful in protecting furniture, wooden frames, ships, automobiles, airplanes or other vehicles of transportation, road signs, pipes and the like. In addition, they increase the adhesion to metals when applied thereto, and also retard the corrosion process.

Thus, compounds of the present invention are also corrosion-inhibiting agents. More specifically, compounds of the present invention are used in inhibiting the corrosion of metals, particularly iron, steel, and ferrous alloys. Compounds of the present invention are employed for inhibiting corrosion in processes which require this protective or passivating coating. They can be used in preventing atmospheric corrosion, underwater corrosion, corrosion in streams, corrosion in chemical industries and underground corrosion.

The corrosion inhibitors contemplated herein find special utility in the prevention of corrosion of pipes or equipment which is susceptible to corrosion. In this embodiment, compounds of the present invention may be directly applied onto the metal surface as is, or as a solution in some carrier liquid, paste or emulsion. Compounds of the present invention may also be combined with the polymerizable corrosion inhibiting agents. For instance, the compounds may be applied as a latex paint to the surface of the metal or metal alloy. The latex paint containing the instant polymers of the present invention can be prepared using techniques well known in the art.

For a better understanding of the present invention together with other and further objects, reference is made to the examples.

EXAMPLE 1

Preparation of Poly(bis-methylimidazolyl) Polymer

Poly(methylmethacrylate) (PMMA) was sifted through a wire mesh with about 1×1 mm holes to remove the larger chunks of PMMA. 9.85 g (98.4 mmol of ester units) of the sifted polymer was then weighed. Tetrahydrofuran was then distilled to remove unwanted impurities from the solvent and two long needles were removed from the 110° C. drying oven and placed in the dry box to cool.

A 500 ml, 3-necked round bottom was flame dried and a stir bar was quickly added. The two outside necks were quickly capped with septa and the middle neck was capped with a powder addition funnel and $14/24$ adapter. The powder addition funnel was carefully flame dried and then capped with two septa. The apparatus was flushed with $N_2$. Thereafter, the sifted PMMA was quickly added to the addition funnel after it had cooled. The apparatus was flushed with $N_2$ again and then kept under $N_2$ pressure. 16.16 g (196.8 mmol) of 1-methylimidazolyl (MeIm), about 2 times the molar amount of the ester units in the PMMA, was added to the round bottom flask through one of the septa. Dry THF (120 ml) from the still was added via a dry needle and dry gas-tight syringe. The methylimidazolyl solution was then cooled in a dry ice/EtOH bath with stirring continuing throughout the cooling process.

79 ml (198 mmol) of 2.5M n-butyl lithium in hexane, an equimolar amount to that of the MeIm, was slowly added to the round bottom via a dry gas-tight syringe. This solution was then stirred for about 1 hour in a dry ice bath.

After a period of time, PMMA was added to the MeIm/BuLi solution with the addition funnel. Thereafter, the reaction mixture was stirred vigorously and allowed to thaw to room temperature over 72 hours.

The foregoing reaction mixture was then quenched by adding 5 ml of water. The contents of the flask, a yellow cloudy suspension over a mass of white-yellow gummy solid, were then emptied into a 1 L beaker. 250 ml of THF was then added to the beaker and the content was stirred vigorously for 15 min. The stirring was then stopped and the insoluble solid was left to settle for 10 min. The supernatant was then decanted off. The above separation procedure was repeated with 200 ml of acetone and then 150 ml of THF. The third time, the material was filtered through a large Buchner funnel. This material was allowed to dry over vacuum. It was then crushed with a mortar and pestil and then washed for 15 min in 150 ml of hot water. The material was again filtered with a buchner funnel and dried over vacuum to obtain 3.58 g of a white powder.

EXAMPLE 2

Preparation of Poly(bis-methylimidazol) Polymer

The polymer was prepared in the same manner as Example 1 except that anhydrous ether was used instead of THF as the reaction solvent. Also, after quenching with water, the product was washed once in a large portion of boiling water and then filtered with a sintered glass funnel to obtain white or clear small granules of the solid polymer.

EXAMPLE 3

Preparation of Poly(bis-methylimidazolyl Styrenyl).

A small quantity of bis-methylimidazolyl styrene (0.02 g) compound and 0.80 g of 60/40 v/v styrene/DVB solution were placed in a small test tube. A very small magnetic stir bar was added to the test tube, and the mixture was then place in a 60° C. oil bath with stirring. One drop of methanol was then added to help dissolve the bis-imidazolyl. 0,005 g (0.5% w/w of the total polymer mass) of VA 061 radical initiator was added to the test tube. Stirring was continued until all materials were dissolved. The stir bar was then removed and the test tube was capped with a septa. This solution was polymerized by placing it in front of a strong UV light source overnight. After polymerization was complete, the test tube was shattered and the polymer removed. It was then crushed with a mortar and pestil into a powder and this powder was washed with MeOH and filtered and dried over vacuum in a sintered glass funnel to make the 20% w/w polymer.

EXAMPLE 4

50% polymer was synthesized using the same procedure as described in Example 3, except that 0.50 g of bis-methylimidazolyl styrene compound and 0.50 g of styrene/DVB solution were used.

EXAMPLE 5

A 100% polymer was synthesized by placing 102 mg of bis-methylimidazolyl styrene compound and 1 mg of VA 061 initiator into a small test tube. A small stir bar and 0.1 ml MeOH were then added to this tube. The mixture was then put in an oil bath at 70° C. After all of the bis-methylimidazolyl styrene compound had dissolved, the stir bar was removed and the solution was kept in the 70° C. bath overnight to polymerize. The polymerized material was collected and crushed in the manner stated above. It was not washed, as the material was soluble in MeOH.

EXAMPLE 6

A polymer was prepared in accordance with Example 1 except that polymerization was initiated by letting the solution set in the 60° C. oil bath over night.

EXAMPLE 7

This polymer was made in the same manner as Example 3 except that ethylene glycol dimethacrylate (EGDMA) was used as a polymer matrix in place of styrene/DVB.

EXAMPLE 8

Bis-methylimidazolyl (508 mg) was placed in 2.00 g of EGDMA in a erlenmeyer flask. This mixture was then heated in a sand bath. 0.173 g (about a ½ molar equivalent of 5) of $Cu(OAc)_2H_2O$ was added to the solution. One ml of methanol was then added to the flask. This mixture was heated some more and then passed through a Hirsch funnel. It was then transferred to a test tube and 9.5 mg of VA 061 radical initiator was added and dissolved. The mixture was then put into a 60° C. oil bath and allowed to polymerize over the weekend. The polymer was then crushed and washed as above to produce a dark blue coarse powder. The powder was then washed in about 5 ml of 6M HCl until no more color could be removed. It was then washed in 5% NaOH solution, at which point the material had a green-yellow tint to it.

EXAMPLE 9

The present example determines the metal ion binding capacity of some of the preferred polymers of the present invention. More specifically, the metal ion binding capacity of polymer produced in Examples 1 and 3 and 7 were determined. The specific metal ions analyzed in this investigation were $Cu^{2+}$, $Pb^{2+}$, $Fe^{2+}$, $Fe^{2+}$ and $Hg^{2+}$. Additionally, the binding capacity of these polymers for $Cu^{2+}$ in the presence of excess amounts of $Cu^{2+}$ and $Mg^{2+}$ were also determined.

The following two analytic procedures were employed in the present invention to analysis the foregoing metal ions.

Analysis of Polymer Prepared by Example 1

Apparatus:

A 3-electrode system with a glassy carbon, rotated disk working electrode was constructed in the lab. It was controlled by a 1/40 horsepower G.K. Heller motor and a Series H motor controller (G.K. Heller Corp., Floral Park, N.Y.) with an external voltage control input. The rotation rate was related to the voltage applied to the control input. This allowed us to switch between two independently selected voltages to obtain two reproducible rotation rates.

A separate voltage was applied to the electrochemical cell. This voltage was applied to the working electrode using a BAS (Bioanalytical Systems, inc.) CV-27 Cyclic Voltammograph. Current output was plotted using a BAS X-Y-Recorder.

The polymer was finely crushed and placed in the tube between two 0.5 micron filters.

Electrodes:

The working electrode was a glassy carbon 3 mm disk which was polished with successively finer polishing paper and finally a 1 micron alumina slurry. The reference electrode was a chloridized silver wire in 3M NaCl. The auxiliary electrode was a polished platinum wire.

Reagents:

Deionized water from a Milli-Q system was used to prepare all solutions. A stock $10^{-3}$M $Cu^{2+}$ solution was made by dissolving clean copper metal in 1.0 mL 15M HCl and diluting to 1.0 L. This was used for all $Cu^{2+}$ solutions and diluted to lower concentrations for daily use. Reagent grade HCl was used as supporting electrolyte.

Procedure:

A 10.0 mL aliquot of 0.1M HCl was placed under the electrode, and pretreatment begun. Pretreatment involved cycling from +1.0 V to −1.0 V twice and holding at each voltage for 10 minutes. Oxygen was purged by placing one nitrogen tube so it bubbled through the solution while a second nitrogen tube remained above the surface to blanket the liquid. After pretreatment and between each run, the electrodes were rinsed with deionized water and dried with a chim-wipe. Each solution was derated for ten minutes before analysis began.

Aliquots of 10.0 mL of $Cu^{2+}$ were pipetted into the centrifuge tube and forced through the flow-cell under pressure. Each aliquot was collected in a plastic weighing bottle. 333 microliters of 3M HCl was added to each aliquot to bring the supporting electrolyte concentration to 0.10M HCl.

A preliminary experiment was run to see what the $Cu^{2+}$ should look like once the polymer was no longer removing copper. A 10.0 mL aliquot of $1.0 \times 10^{-5}$M copper (not exposed to the polymer) was de-aerated. The nitrogen tubes remained in place and a potential of −0.5 V was applied. The rotation rate was switched between preselected slow and fast rates a few times, holding at each rate for approximately 20–30 seconds.

This procedure was repeated with each of the filtrates.

A calibration curve was made following the same basic guidelines. The sample value was compared to this curve and concentration of each filtrate determined. These values were combined to calculate the capacity. (See Table 1).

Analysis of PMMA Polymers

Apparatus:

Ultraviolet absorption spectra were obtained using a Hewlett Packard 8452A Diode Array Spectrophotometer. Voltammetric spectra were measured on a BAS 100 W Program with a BAS 100 B controlling module, EG&G Parc Cell Stand. The electrodes are the same as above, a glassy carbon working electrode, an AgCl reference electrode and a platinum wire as an auxiliary electrode.

Reagents: 0.2M $Cu^{2+}$ and 0.2M $Fe^{3+}$ solutions were prepared by dissolving reagent grade metal nitrates in distilled water. 100 mL of the $Cu^{2+}$ solution were removed and appropriate amounts of calcium nitrate and magnesium nitrate added to bring the concentration of each to 0.1M. 3.0 mg/100 mL solution of $HgCl_2$ was prepared using distilled water. 100 ml of 5% KSCN solution was made up by weighing out 5.02 g of KSCN and added distilled water until it weighed 100 g. 0.02M $Pb^{2+}$ solution was prepared by dissolving Pb metal in concentrated nitric acid and diluting with deionized water.

Procedures:

$Cu^{2+}$ test:

A known amount, typically 1 gm, of polymer was weighed out and placed in a polyethylene weigh bottle with 11.5 mm stir bar. 50 mL of 0.2M $Cu^{2+}$ solution was added and the solution was stirred on a rotating stir plate overnight. Approximately 5 mL of this solution was then removed and passed through a 0.45 micron filter. A plastic 1-cm cuvette was rinsed with some of this solution which was discarded and more solution added. This sample was scanned from 200–820 nm. The peak at 800 nm was recorded. This was compared to a calibration curve made using dilutions of the standard $Cu^{2+}$ solution. The capacity was then calculated to the value shown in Table 1.

$Cu^{2+}$ in the presence of $Ca^{2+}$ and $Mg^{2+}$ test:

A known amount, typically 1 gm, of the polymer was weighed out and placed in a polyethylene weigh bottle with a 11.5 mm stir bar. 50 mL of the 0.1M $Ca^{2+}$, 0.1M $Mg^{2+}$ was scanned. Then the sample, filtered as above was scanned. This value was compared to the copper calibration curve and capacity calculated. (See Table 1).

$Fe^{3+}$ test:

A known amount, typically 1 gm, of the polymer was weighed out and placed in a polyethylene weigh bottle with a 11.5 mm stir bar. 50 mL of 0.02M $Fe^{3+}$ was added and the solution stirred overnight on a rotating stir plate. Approximately 5 mL of this solution was then filtered through a 0.45 micron filter. This sample was scanned from 500–800 nm and the absorption at 654 nm was recorded. This value was compared to a calibration curve made up by diluting the standard $Fe^{3+}$ solution and the capacity was calculated. (See Table 1).

$Hg^{2+}$ test:

A known amount, typically 1 gm, of polymer was weighed out into a polyethylene weigh bottle. 50 mL of the mercuric chloride solution were added along with a 11.5 mm stir bar. The solution was stirred on a rotating stir plate overnight. Blank of 40 mL of 5% KSCN solution diluted to 100 mL was scanned. 25 mL of mercuric chloride solution was then filtered and placed in 50 mL volumetric flask. 20 mL of KSCN solution was added and volume brought up to the mark with distilled water. This was placed in a 1 cm quartz cuvetter and scanned. The value at 282 nm was recorded. This was compared to a calibration curve made up by varying the amount of the standard mercuric chloride solution and distilled water while keeping the amount of KSCN constant. From this curve the capacity was calculated. (See Table 1).

Control Test:

A known amount, typically 1 gm, of nonfunctionalized PMMA polymer was weighed out and placed in a polyethylene bottle with a stir bar. 50 mL of the standard $Cu^{2+}$ solution was added and stirred overnight on the rotating stir plate. A small amount of this solution was removed and filtered. It was scanned and the value at 800 nm recorded. This was compared to the calibration curve and showed no copper removal by the nonfunctionalized polymer.

$Pb^{2+}$ test:

A known amount, typically 1 gm, of the polymer was weighed out and placed in a polyethylene weigh bottle with a 11.5 mm stir bar. 50 mL of 0.2M $Pb^{2+}$ was added and the solution stirred overnight on the magnetic stir plate. The sample was passed through 0.45 micron filter. 1 mL of sample was diluted to 100 mL using deionized water in a volumetric flask. The glassy carbon electrode was polished with an alumina suspension and rinsed with deionized water. The dilute sample was purged with nitrogen for ten minutes. It was scanned from −1000 mV to −100 mV on the DPT cycle. The peak at −348 mV was recorded. This was compared to a calibration curve. The values for the curve were found by scanning $5 \times 10^{-5}$M $Pb^{2+}$ solution prepared from standard after purging for ten minutes. This solution was then spiked for each successive scan and purged for two minutes. The calculated capacity is shown in Table 1.

The results of this experiment are shown in Table 1. The data in this table illustrates that the polymers of the present invention are capable of binding metal ions efficiently. Moreover, the polymer prepared in accordance with the procedure described in Example 1 exhibited an extremely high capacity or binding $Cu^{2+}$, $Pb^{2+}$ and $Fe^{2+}$ ions. This values report for this example are higher then those previously reported using commercial available ion exchange resins.

TABLE 1

Binding Capacity of Different Polymers for Various Metal Ions.

| Polymer Description | Binding Capacity (in meq/g) | | | | |
|---|---|---|---|---|---|
| | $Cu^{2+}$ | $Cu^{2+}$* | $Pb^{2+}$ | $Fe^{3+}$ | $Hg^{2+}$ |
| See Example 1 | 5.04 | — | 3.97 | 5.38 | 0.055 |
| See Example 3 | 0.0057 | — | — | — | — |
| See Example 1** | 1.44 | 1.39 | 1.09 | — | — |

*Denotes that the measurement was conducted in the presence of excess $Ca^{2+}$ and $Mg^{2+}$.
**Same procedure as Example I except that the MeIm/BuLi solution was added to solid PMMA.

EXAMPLE 10

1,10-bis(1-methylimidazol-2-yl)-1,10-didecanol,2.

To a 2 L flame-dry round-bottom flask with magnetic stir bar 375 mLs of anhydrous THF is added via canula after establishing $N_2$ flow. In a second 1 L flame-dry round-bottom flask with magnetic stir bar and under $N_2$ positive pressure, 650 mLs of anhydrous THF is added via canula.

50.99 g (0.621 mol) of 1-methylimidazole is then added via syringe to the 1 L flask. This flask is then cooled to −78° C. when immersed in a CO$_2$/EtOH bath. To the 2 L flask 37.08 g (0.155 mol) sebacoyl chloride is added via syringe; this solution is a brown color. Once the 1-methylimidazole solution is cooled, 298 mLs (0.744 mol) of 2.5M n-Butyllithium (in hexanes) is added carefully via syringe. After the n-BuLl is added, the bath is restocked as the reaction mixture stirs for 2.5 hours. At that point, the methylimidazole carbanion solution (a yellow/orange solution) is dripped into the pre-cooled (−78° C.) sebacoyl chloride solution via canula. During transfer, the mixture in the destination flask turns a creamy, light yellow color and eventually a butterscotch color upon complete transfer, 1 hour later. Some yellow solids are also present on the flask bottom. The reaction mixture is kept at −78° C. for 1.5 hours, then allowed to reach room temperature overnight. In the morning, the reaction mixture is quenched by removal of the septum and subsequent dropwise addition of 15 mLs distilled H$_2$O. The vessel is swirled carefully by hand to assist the quenching. The reaction solvents are then removed in vacuo in a 40° C. water bath. The butterscotch residue is dissolved in 600 mLs of saturated NaCl solution. The solution is extracted with five aliquots of 250 mLs methylene chloride. The extract is dried over anhydrous sodium sulfate then filtered. The methylene chloride is removed in vacuo in a 40° C. water batch to leave a gel-like red/brown residue. The residue is washed with acetone and filtered to isolate 2 as a light tan powder. $^1$H NMR (300 MHz, CDCl$_3$): δ6.9410, 6.9369 (d, CH, 4H, J=1.23 Hz), 6.7980, 6.7940 (d, CH, 4H, J=1.20 Hz), 3.2991 (s, CH$_3$, 12H), 2.4959 (m, CH$_2$, 4H), 1.994 (s, OH, 2H), 1.2568 (m, CH$_2$, 12H). $^{13}$C NMR (300 MHz, CDCl$_3$): δ147.8606, 125.7522, 123.3692, 71.7483, 38.4278, 33.4419, 29.4671, 22.6524. IR (NaCl, cm$^{-1}$): 3063.90(m), 2994.58(m), 2936.82(m), 1723.84(s), 1585.22(m), 1435.04(m), 1377.28(s), 1279.09(s), 1232.88 (s), 909.42(s), 759.25(m), 600–400(m). M.P.=169.8° C.

EXAMPLE 11

Bis(1-vinylimidazol-2-yl) ketone, (BVK)

A flame-dry round-bottom flask with magnetic stir bar is cooled under N$_2$ flow. 180 mLs anhydrous THF is added via canula and positive N$_2$ pressure is established. 7.39 g (78.5 mmol) of 1-vinylimidazole (a light yellow liquid) is added via syringe. The vessel is then cooled to −78° C. by immersion is a CO$_2$/EtOH bath. Once cool, 32 mLs of 2.5M n-butyllithium is carefully added via syringe. The reaction is allowed to stir for approximately 1 hour while −78° C. is maintained. Meanwhile a second 500 mL flame-dry round-bottom flask is cooled under N$_2$ flow and 100 mLs of anhydrous THF are added to it via canula. Positive N$_2$ pressure is established. This is followed by syringe addition of 3.54 g (39.3 mmol) dimethyl carbonate. The second flask is cooled to −78° C. in a CO$_2$/EtOH bath. After the 1 hour has elapsed in the first vessel's reaction, the contents of the first flask (a greenish/orange solution) are transferred via canula to the second flask. The transfer is done dropwise over a 1 hour period. No signs of a color change occur in the destination flask. The reaction mixture is allowed to stir overnight while warming to 25° C. In the morning the reaction mixture is quenched by lifting of the septum and adding excess solid CO$_2$. This is done slowly. Yellow solids precipitate out of the solution. The solvents are then removed in vacuo with a 25° C. water bath. The white residue is dissolved in 250 mLs of saturated NaCl solution. Much of the solid residue does not dissolve. The brine solution is filtered through a Büchner funnel to collect the light yellow crystals. The brine solution is then extracted with three aliquots of 100 mLs methylene chloride. The extract is dried over anhydrous sodium sulfate and filtered through a fluted filter. The methylene chloride is removed in vacuo with a 25° C. water bath to leave light yellow crystals. The light yellow crystals are washed with diethyl ether to leave a white solid; or they can be recrystallized from boiling diethyl ether to isolate clear crystals. $^1$HNMR (300 MHz, CDCl$_3$): δ7.7167, 7.6179, 7.6645, 7.6355 (q, CNH, 2H, J=8.705 Hz and 7.001 Hz), 7.4710, 7.4671 (d, CH, 2H, J=1.16 Hz), 7.3457, 7.3423 (d, CH, 2H, J=1.01 Hz), 5.3940, 5.3888, 5.3418, 5.3365 (d of d, CH$_2$, 2H, J=14.08 Hz and 1.59 Hz), 5.0751, 5.0698, 5.0462, 5.0408 (d of d, CH$_2$, 2H, J=7.08 Hz and 1.59 Hz). $^{13}$C NMR (300 MHz, CDCl$_3$): δ173.9390, 141.9383, 131.3468, 130.9122, 121.2263, 105.4057, IR (NaCl, cm$^{-1}$): 3167.87–2994.581 m); 1723.84 (s); 1660.31(s); 1510.13, 1440.82, 1394.01(m); 1313.75, 1279.09, 1300(m); 1140.46 (m); 1094.25(s); 1059.59(s); 967.18,944.07, 886.31(m). M.P.=133.0° C.

EXAMPLE 12

Synthesis of 1-Methylimidazole Anion

The materials needed for synthesis of the anion are 1-methylimidazole and 2.5M butyllithium in hexanes reacted in anhydrous THF at a temperature of −78° C. achieved by a dry ice/ethanol bath. A 2.2 molar equivalent of 1- methylimidazole and butyllithium relative to the molar amount of starting material is needed for the synthesis. The amount of anhydrous THF needed is determined by the ratio of 8 mL anhydrous THF/1 g 1-methylimidazole. A round bottom flask is equipped with a stir bar, and the same is flame dried. A septum is placed on the round bottom flask immediately after the drying is completed. The round bottom flask and stir bar is cooled with N$_2$(g) flow and when cooled, positive N$_2$ pressure is maintained. 1-methylimidazole is added with a dried, cooled syringe to the anhydrous THF added with a dry canula. The solution is cooled for about fifteen minutes until a temperature of −78° C. is reached. The volume of 2.5M butyllithium is then calculated from the moles required, and the calculated amount of butyllithium added slowly with a dry syringe. The solution is allowed to react at −78° C. for at least one hour. The anion solution should be dark yellow/orange color.

In the experiments listed hereinabove and hereinbelow, this procedure was followed except where noted.

EXAMPLE 13

Bis-methylimidazole Functionalized Phthalic Anhydride

An amount of 5.00 g (0.03376 mol) of phthalic anhydride was added to a dried, N$_2$ cooled 250 mL round bottom flask with a stir bar by quickly removing the septum, pouring the solid through a funnel, and replacing the septum. A positive N$_2$ pressure was maintained. An addition of about 100 mL of anhydrous THF was added to the 250 mL round bottom flask with a dry canula and stirred for about ten minutes to allow the phthalic anhydride to dissolve. A 1-methylimidazole anion solution was synthesized with 5.82 g (0.07090 mol) of 1-methylimidazole and about 28.3 mL (0.07090 mol) of 2.5M n-butyl lithium in about 100 mL anhydrous THF. The phthalic anhydride solution was transferred with a dry canula while maintaining the reaction at −78° C. The reaction was allowed to stir overnight (about thirteen hours) at room temperature. In the morning, the reaction was quenched with 0.61 g (0.03376 mol) of distilled water which is an equivalent molar amount equal to the molar amount of phthalic anhydride. The contents of the reaction vessel were put into a crystallizing dish and allowed to evaporate, and an off white solid remained. The off white solid was found to be soluble in water, but not in any common organic solvents. $^1$H NMR (300MHz, D$_2$O) 3.33 (s, 6H), 6.10 (d, J=7.7 Hz, 1H), 6.64 (s, 2H), 6.94 (s, 2H), 7.14 (t, J=7.23 Hz, 1H), 7.25 (t, J=7.53 Hz, 1H), 7.65 (d, J=6.21, 2H).

EXAMPLE 14

Bis-methylimidazole Functionalized Styrene/Maleic Anhydride (75/25) Copolymer Since only the maleic anhydride part of the copolymer can be functionalized, the molar amount of starting material must be calculated based on the 25% of maleic anhydride units in the copolymer. Therefore, in a 10 g sample of starting material, there is 2.5 g (0.02549 mol) of maleic anhydride that will be functionalized. The 2.5 g (0.02549 mol) of maleic anhydride units (10.01 g of copolymer) was added to a dried, N$_2$ cooled 250 mL round-bottom flask with a stir bar by quickly removing the septum, pouring the solid through a funnel, and replacing the septum. A positive N$_2$ pressure was maintained. An addition of about 200 mL of anhydrous THF was added to the 250 mL round-bottom flask with a dry canula and stirred for about ten minutes to allow the copolymer to dissolve. A 1-methylimidazole anion solution was synthesized with 4.61 g (0.05608 mol) of 1-methylimidazole and about 22.4 mL (0.05608 mol) of 2.5M butyllithium in about 100 mL anhydrous THF. The copolymer solution was transferred with a dry canula while maintaining the reaction at −78° C. The reaction was allowed to stir overnight (about thirteen hours) at room temperature. In the morning, the reaction was quenched with a couple of milliliters of distilled water. The reaction vessel was then rotoevaporated at approximately 70° C. to give a yellow solid. The solid that remained was dried in a vacuum oven without heat for two and a half days. The solid was found to be water insoluble. After which time, the solid was two shades of yellow. Three 0.75 g (approximate weight) samples of this solid were washed. The first sample was washed with distilled water, the second with 10% NaOH and distilled water, and the third with saturated NaCl and distilled water. The original yellow solid was found to be soluble in water. The sample washed with saturated NaCl became a lighter yellow color.

EXAMPLE 15

Bis-methylimidazole Functionalized Ethylene/ Maleic Anhydride (50/50 Copolymer)

Since only the maleic anhydride part of the copolymer can be functionalized, the molar amount of starting material must be calculated on the 50% of maleic anhydride units in the copolymer. Therefore, in a 10 g sample of starting material, there is 5.0 g (0.05099 mol) of maleic anhydride units that will be functionalized. A 1-methylimidazole anion solution was synthesized in 500 mL round-bottom flask that had two $^{24}$/$_{40}$ necks with about 9.23 g (0.1122 mol) of 1-methylimidazole and about 56 mL (0.01122 mol) of 2.5M n-Butyl lithium in about 300 mL anhydrous THF. An amount of 10.00 g of the copolymer (0.05099 mol of maleic anhydride units) was added to the anion solution with a solid addition apparatus that was placed in the second neck of the 500 mL round bottom flask. The addition of the copolymer (a white solid) was done while maintaining the reaction at −78° C. The reaction was allowed to stir overnight (about thirteen hours) at room temperature. In the morning, it was observed that not all of the copolymer reacted by way of a white solid (the copolymer) still stirring in the reaction vessel. The reaction was quenched with 2.02 g (0.1122 mol) of distilled water which is an equivalent molar amount equal to the molar amount of 1-methylimidazole. After about 45 minutes, there were two layers of solid material and a top layer of solvent. The solids were light brown and yellow. The solvent layer was decanted off, while half of the remaining solids were filtered with fluted filter paper. The filtered half of the solids were emptied into a crystallizing dish. The other half of the solids were also filtered and scraped into the same crystallizing dish. The crystallizing dish was dried in a vacuum oven for about thirteen hours at 60° C. The solids were now white and brown colored, and were found to be water soluble. The solids were washed four times with tech. grade diethyl ether and dried for 45 minutes in a vacuum oven at 21 in. Hg vacuum. Once removed from the oven, the solid was a light yellow color and was found to be slightly hygroscopic. Three 0.20 g samples of this diethyl ether washed solid were washed in fluted filter paper. The first sample was washed with distilled water to become clear/white and had a cream-of-wheat-like texture. The second sample was soaked with 10% NaOH and washed with distilled water to become clear with a very light yellow tint. This second sample increased in size after washing with water and had the texture of cream-of-wheat. The third sample was soaked in saturated NaCl and washed with distilled water to become a clear/white color with a slight cream-of-wheat-like texture. The third sample also increased in size after washing with water. The three samples were dried in vacuum oven without heat overnight (about thirteen hours). All three samples looked like a gel after being dried overnight, and they eventually dried to solids without changing color after a period of days of sitting out in the open atmosphere.

EXAMPLE 16

Bis-methylimidazole Functionalized Methacryloyl Chloride Polymer

Since the methacryloyl chloride is a polymer the molar amount of reactants must be determined for a molar amount of individual methacryloyl chloride units. The molecular weight of each unit is 104.54 g/mol. Therefore, in a 5 g sample of starting material, there is 0.04783 mol of methacryloyl chloride units that will be functionalized. A 1-methylimidazole anion solution was synthesized in 500 mL round-bottom flask that had two 24/40 necks with 8.63 g (0.1052 mol) of 1-methylimidazole and about 42.0 mL (0.01052 mol) of 2.5M butyllithium in about 150 mL anhydrous THF. An amount of 5.0 g (0.04783 mole of methacryloyl chloride units) of the polymer was added to the anion solution with a solid addition apparatus that was placed in the second neck of the 500 mL round bottom flask. The addition of the polymer was done while maintaining the reaction of −78° C. The reaction was allowed to stir overnight (about thirteen hours) at room temperature. In the morning, it was observed that about 50 mL of solvent had evaporated most likely through one of the parafilmed seals of the reaction vessel. The reaction was quenched with 0.86 g (0.4783 mol) of distilled water which is an equivalent molar amount equal to the a molar amount of methacryloyl chloride units. The reaction mixture was rotoevaporated to yield an extremely dark green (almost black) solid that was water soluble. The remaining solid was dissolved in absolute thianol and allowed to sit for about thirteen hours at room temperature. Two layer formed. The top layer was a creamy white solid in a seemingly yellow solvent, and the bottom layer was a black and white gunk. The top layer was decanted off. This top layer was allowed to evaporate to dryness and found to be a tan colored solid that was water soluble and hygroscopic. The bottom layer was a black gunk with a thin white layer on top of it. When scraped with a spatula, this bottom layer became string-like that would be similar to a polymer. The bottom layer was then allowed to evaporate to dryness in the open air and was found to be a hard coating that was black on the bottom and white on the top.

EXAMPLE 17

Bis-methylimidazole Functionalized Methacryloyl Chloride Polymer 25% in Dioxane

Since only the methacryloyl chloride polymer can be functionalized, the molar amount of starting material must be calculated based on the 25% of methacryloyl chloride polymer that is in dioxane. Therefore, in a 10 g sample of starting material, there is 2.5 g (0.02392 mol) of methacryloyl chloride polymer that will be functionalized. This calculation is based on one methacryloyl chloride unit having a molecular mass of 105.54 g/mol. A 1-methylimidazole anion solution was synthesized in about 100 mL anhydrous THF with 4.95 g (0.05979 mol) of 1-methylimidazole and in this case, an amount of 2.5M butyllithium that was equal to 1.2 times the molar amount of 1-methylimidazole. The amount of 2.5M butyllithium added was about 28.7 mL (0.0715 mol). A 10.00 g sample of polymer solution (0.02392 mole of methacryloyl chloride) was added to the anion solution with a syringe while maintaining the reaction at $-78°$ C. The reaction was allowed to stir overnight (about thirteen hours) at room temperature. In the morning, the reaction was quenched with 0.43 g of distilled water and allowed to stir for about 75 minutes. At this time, the reaction vessel was swished around and allowed to stir another three hours. The contents of the reaction vessel were added to a beaker containing 50 mL of distilled water. This caused a red solid to precipitate on the bottom of the reaction vessel and left only a slightly yellowish-brown liquid on top. After being allowed to sit out in the atmosphere for two days, an orangish-cream colored solid was floating on top of a red liquid. When tested for water solubility, this orangish-cream colored solid formed a yellow liquid and a white solid. The contents of the beaker were allowed to evaporate and then dried in a vacuum oven at about 40° C. and at about 22 in. Hg vacuum for about 24 hours. The solid looked like bacon bits.

EXAMPLE 18

Bis-methylimidazole Functionalized Styrene/Maleic Anhydride (50/50) Copolymer

Since only the maleic anhydride part of the copolymer can be functionalized, the molar amount of starting material must be calculated based on the 50% of maleic anhydride units in the copolymer. Therefore, in a 15 g sample of starting material, there is 7.5 g (0.07648 mol) of maleic anhydride units that will be functionalized. An amount of 15.00 g (0.07648 mol of maleic anhydride units) of copolymer was added to a dried, $N_2$ cooled 500 mL round-bottom flask with a stir bar by quickly removing the septum, pouring the solid through a funnel, and replacing the septum. A positive $N_2$ pressure was maintained. An addition of about 200 mL of anhydrous THF was added to the 500 mL round-bottom flask with a dry canula and stirred for about twenty minutes to allow the copolymer to dissolve. A 1-methylimidazole anion solution was synthesized with 13.82 g (0.1683 mol) of 1-methylimidazole and about 67.3 mL (0.1683 mol) of 2.5M butyllithium in about 300 mL anhydrous THF. The copolymer solution was transferred into the anion solution with a dry canula while maintaining the reaction at $-78°$ C. The reaction was allowed to stir overnight (about thirteen hours) at room temperature. The reaction was quenched with 4.55 g (0.2525 mol) of distilled water which is 1.5 times the molar equivalent amount of the copolymer. The contents of the reaction vessel were roto-evaporated at 55° C. to give a butterscotch yellow solid that was water soluble. The solid was emptied into a crystallizing dish and put into a vacuum oven to dry overnight (about thirteen hours) at about 40° C. and at about 23 in. Hg vacuum. The solid was still mostly butterscotch yellow, but there was also a small about of whit solid and a small amount of a lighter yellow solid.

The above preferred embodiments and examples are given to illustrate the scope and spirit of the present invention. These embodiments and examples will make apparent to those skilled in the art other embodiments and examples. These other embodiments and examples are also within the contemplation of the present invention. Therefore, the present invention would be limited only by the appended claims.

What is claimed is:

1. A compound of the formula:

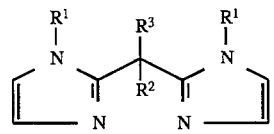

or a salt thereof wherein $R^1$ is hydrogen, lower alkyl, lower alkenyl, lower alkynyl, or lower alkoxy;

$R^2$ is lower alkoxy or hydroxy or acroyloxy;

$R^3$ is lower alkynyl, lower alkoxy, halogen, sulfato, nitro, lower alkanoyl, carboxy, formyl, lower carbalkoxy;

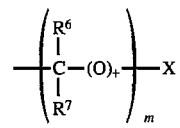

or

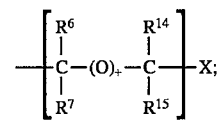

$R^6$ is hydrogen or lower alkyl;

$R^7$ is lower alkynyl, lower alkoxy, sulfato, lower alkanoyl, carboxy, lower carbalkoxy, or formyl; or $R^6$ and $R^7$ taken together with the carbon atom to which they are attached form

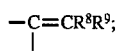

$R^8$ is hydrogen or lower alkyl;

$R^9$ is

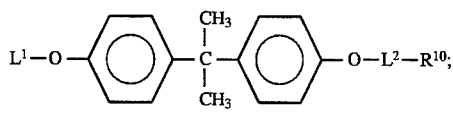

$L^1$ and $L^2$ are independently

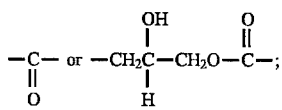

$R^{10}$ is

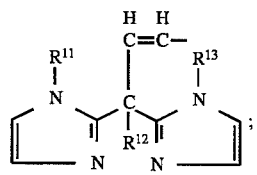

$R^{11}$ and $R^{13}$ are independently hydrogen, lower alkyl, lower alkenyl, lower alkynyl or lower alkoxy;

$R^{12}$ is hydroxy or lower alkoxy;

$R^{14}$ and $R^{15}$ are independently hydrogen, lower alkyl, lower alkenyl, lower alkanoyl, formyl, carboxy, lower carbalkoxy, or $R^{14}$ and $R^{15}$ taken together with the carbon atom to which they are attached form

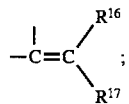

$R^{16}$ is hydrogen or lower alkyl;

$R^{17}$ is

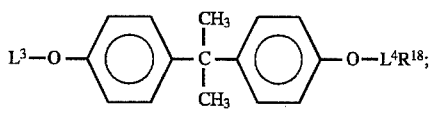

$L^3$ and $L^4$ are independently

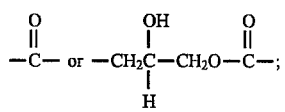

$R^{18}$ is

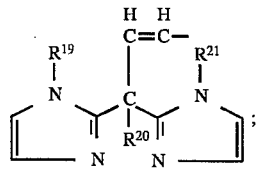

$R^{19}$ and $R^{21}$ are independently hydrogen, lower alkyl, lower alkenyl, lower alkenyl, or lower alkoxy;

$R^{20}$ is hydroxy or lower alkoxy;

X is hydrogen, lower alkyl, lower alkenyl, lower alkynyl, lower alkoxy, halogen, sulfato, nitro, lower alkanoyl, formyl, carboxy, lower carbalkoxy;

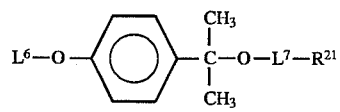

or

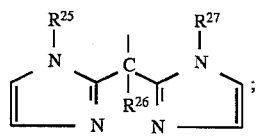

$L^6$ and $L^7$ are independently

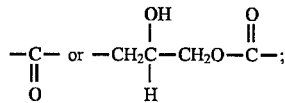

$R^{21}$ is

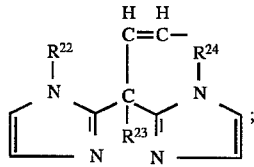

$R^{22}$ and $R^{24}$, $R^{25}$ and $R^{27}$ are independently hydrogen, lower alkyl, lower alkenyl, lower alkynyl or lower alkoxy;

$R^{23}$ and $R^{26}$ are independently hydroxy, lower alkoxy or lower alkyl;

m=1–15;

t=0 or 1; and l=0–5.

2. The compound or salt of claim 1 wherein $R^1$ is hydrogen, lower alkyl, lower alkenyl, lower alkynyl or lower alkoxy;

$R^2$ is lower alkoxy or hydroxy or acroyloxy;

$R^3$ is

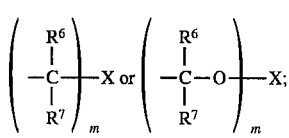

$R^6$ and $R^7$ are taken together with the carbon to which they are attached form

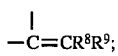

$R^8$ is hydrogen or lower alkyl;
$R^9$ is

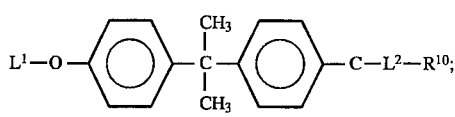

$L^1$ and $L^2$ are independently

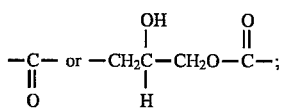

$R^{10}$ is

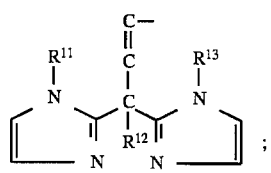

$R^{11}$ and $R^{13}$ are independently hydrogen or lower alkyl;
$R^{12}$ is hydroxy, lower alkoxy or acroyloxy;
X is hydrogen, lower alkyl or

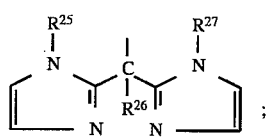

$R^{25}$ and $R^{27}$ are independently hydrogen lower alkyl, lower alkenyl or lower alkynyl; and $R^{26}$ is hydroxy or lower alkoxy or acryloxy; and m is 1–15.

3. The compound according to claim 2 wherein $R^1$ is hydrogen or lower alkyl.

4. The compound according to claim 3 wherein lower alkyl is methyl.

5. The compound according to claim 4 wherein $R^2$ is hydroxy, methoxy or acroyloxy.

6. The compound according to claim 5 wherein $R^3$ is

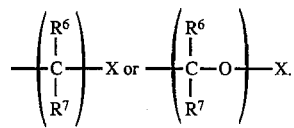

7. The compound according to claim 6 wherein $R_3$ is

wherein
X is hydrogen;
$R^8$ is hydrogen or lower alkyl;
$L^1$ and $L^2$ are

and $R^{11}$ are independently hydrogen or lower alkyl; and
$R^{12}$ is lower alkoxy or hydroxy.

8. The compound according to claim 7 wherein $R^{11}$ and $R^{13}$ are the same.

9. The compound according to claim 7 wherein $R^1$, $R^{11}$, and $R^{13}$ are the same.

10. The compound according to claim 7 wherein $R^1$, $R^{11}$, and $R^{13}$ are lower alkyl or hydrogen.

11. The compound according to claim 10 wherein $R^1$, $R^{11}$, and $R^{13}$ are methyl.

12. The compound according to claim 2 wherein lower alkoxy is methoxy.

13. The compound according to claim 1 wherein $R^1$ is lower alkyl; $R^2$ is OH or lower alkoxy or acroyloxy; $R^3$ is

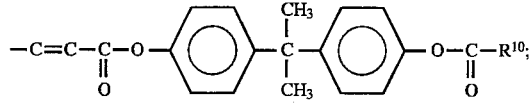

$R^{10}$ is

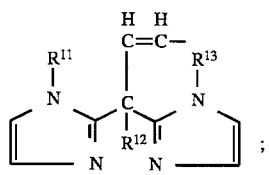

$R^{11}$ and $R^{13}$ are independently lower alkyl
$R^{12}$ is $R^2$, and
X is hydrogen or lower alkyl.

14. The compound according to claim 1 wherein $R^{11}$ and $R^{13}$ and $R^1$ are the same.

15. The compound according to claim 14 wherein $R^{11}$, $R^{13}$ and $R^1$ are methyl.

16. The compound according to claim 13 wherein $R^{12}$ and $R^2$ are both hydroxy.

17. The compound according to claim 13 wherein $R^1$, $R^{13}$ and $R^{11}$ are the same and $R^{12}$ and $R^2$ are both hydroxy.

18. The compound according to claim 17 wherein $R^1$, $R^{13}$ and $R^1$ are both methyl.

19. A compound of the formula:

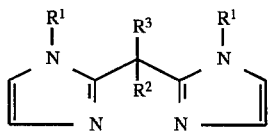

or a salt thereof wherein $R^1$ is independently hydrogen, lower alkyl, lower alkenyl, lower alkynyl or lower alkoxy;

$R^2$ is lower alkoxy or hydroxy or acroyloxy;

$R^3$ is

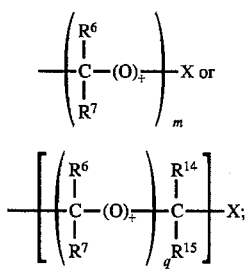

$R^6$ and $R^7$ are independently hydrogen, lower alkyl, lower alkenyl, lower alkynyl, lower alkoxy, sulfato, lower alkanoyl, carboxy, lower carbalkyl or formyl; or $R^6$ and $R^7$ taken together with the carbon atom to which they are attach form $-C=CR^8R^9$;

$R^8$ and $R^9$ are independently hydrogen, lower alkyl, lower alkenyl, lower alkynyl, carboxy or carbalkoxy;

$R^{14}$ and $R^{15}$ are independently hydrogen, lower alkyl, lower alkenyl, lower alkynyl, lower alkoxy, halogen, sulfato, nitro, lower alkanoyl, formyl, carboxy, lower carbalkoxy, or $R^{14}$ and $R^{15}$ taken together with the carbon atom to which they are attached form

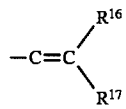

$R^{16}$ and $R^{17}$ are independently hydrogen or lower alkyl;

X is

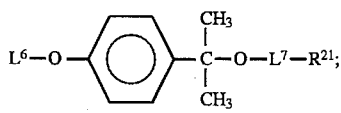

$L^6$ and $L^7$ are independently

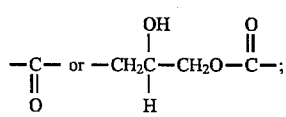

$R^{21}$ is

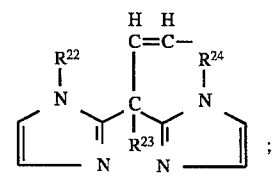

$R^{22}$ and $R^{24}$ are independently hydrogen, lower alkyl, lower alkenyl, lower alkynyl, or lower alkoxy;

$R^{23}$ is hydroxy or lower alkoxy;

m is 0–15;

t is 0 or 1; and q is 0 or 1.

20. The compound according to claim 19 wherein $R^1$ is hydrogen or lower alkyl.

21. The compound according to claim 20 wherein lower alkyl is methyl.

22. The compound according to claim 19 $R^3$ is

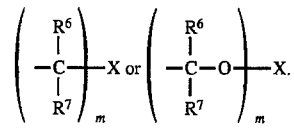

23. The compound according to claim 22 wherein $R^6$ and $R^7$ are independently hydrogen or lower alkyl or $R^6$ or $R^7$ are taken together with the carbon to which they are attached so that $R^3$ becomes

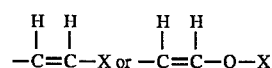

and

X is

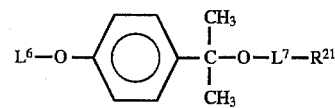

or

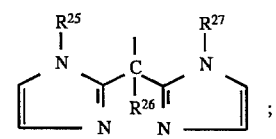

$L^6$ and $L^7$ are independently

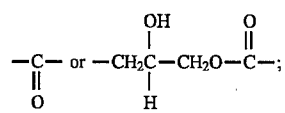

$R^{22}$ and $R^{24}$ are independently hydrogen or lower alkyl, and $R^{23}$ is hydroxy or lower alkoxy.

24. The compound according to claim 23 wherein $R^3$ is C=C—X or C=C—O—X.

25. The compound according to claim 22 wherein $R^{22}$, $R^{24}$ and each $R^1$ are the same.

26. The compound according to claim 22 wherein $R^{23}$ and $R^2$ are the same.

27. The compound according to claim 25 wherein $R^{22}$, $R^{24}$ and each $R^1$ are lower alkyl.

28. The compound according to claim 27 wherein $R^{22}$, $R^{24}$ and $R^1$ are methyl.

29. The compound according to claim 22 wherein $R^{23}$ and $R^2$ are hydroxy.

30. The compound according to claim 19 wherein $R^1$ is lower alkyl; $R^2$ is OH or lower alkoxy;

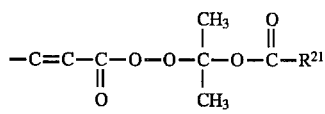

and $R^{21}$ is

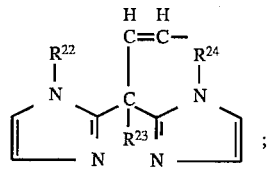

31. The compound according to claim 24 wherein $R^1$, $R^{22}$ and $R^{24}$ are the same.

32. The compound according to claim 31 wherein $R^1$, $R^{22}$ and $R^{24}$ are lower alkyl.

33. The compound according to claim 32 wherein $R^1$, $R^{22}$ and $R^{24}$ are methyl.

34. The compound according to claim 30 wherein $R^{23}$ and $R^2$ and $R^{23}$ are OH.

35. The compound according to claim 34 wherein $R^2$ and $R^{23}$ are OH.

36. The compound according to claim 30 wherein $R^1$ is methyl; $R^2$ is OH; $R^{22}$ and $R^{24}$ are methyl and $R^{23}$ is OH.

* * * * *

UNITED STATES PATENT AND TRADEMARK OFFICE
CERTIFICATE OF CORRECTION

PATENT NO. : 5,637,728
DATED : June 10, 1997
INVENTOR(S) : J. Thomas Ippoliti, et al.

It is certified that error appears in the above-identified patent and that said Letters Patent is hereby corrected as shown below:

Column 2, line 40: "1-OH" should read -- $\ell$-OH --

Column 5, line 2: "1=0" should read -- $\ell = 0$ --

Column 5, line 20: delete "15"

Column 8, line 49: "preferred" should read --referred--

Column 9, line 13: "$R^{12}$" should read -- $R^{13}$ --

Column 9, line 52: "$R^{21}$" should read --$R^{21}$--

Column 9, line 53: "$R^{0}$" should read --$R^{20}$--

Column 10, line 19: " --CR " should read -- --C=CR --

Column 17, line 13: "$CH_3$" should read --$CH_2$--

Column 19, line 50: after "ethanol" delete --.--

Column 21, lines 46 & 47: "$H_2$" should read --$H_2O$--

Column 26, line 12: "1 X 1" should read --1 mm X 1--

Column 26, line 39: "PMMAwas" should read --PMMA was--

Column 27, line 9: "0,005" should read --0.005--

UNITED STATES PATENT AND TRADEMARK OFFICE
CERTIFICATE OF CORRECTION

PATENT NO. : 5,637,728

DATED : June 10, 1997

INVENTOR(S) : J. Thomas Ippoliti, et al.

Page 2 of 3

It is certified that error appears in the above-identified patent and that said Letters Patent is hereby corrected as shown below:

Column 28, line 27: "inc." should read --Inc.--

Column 29, line 18: "Reagents:..." should begin a new paragraph.

Column 32, line 2: "crystals-" should read --crystals.--

Column 32, line 3: "chloride-" should read --chloride.--

Column 32, line 10: "7.6179" should read --7.6879--

Column 34, line 55: "mole" should read --mol--

Column 36, line 22: "whit" should read --white--

Column 38, line 61, Claim 1: "1=0" should read -- $\ell$ =0--

Column 39, line 65, Claim 5: "claim 4" should read --claim 2--

Column 40, line 6, Claim 6: "claim 5" should read --claim 2--

UNITED STATES PATENT AND TRADEMARK OFFICE
CERTIFICATE OF CORRECTION

PATENT NO. : 5,637,728
DATED : June 10, 1997
INVENTOR(S) : J. Thomas Ippoliti, et al.

It is certified that error appears in the above-identified patent and that said Letters Patent is hereby corrected as shown below:

Column 40, line 9, Claim 7: "claim 6" should read --claim 2--

Column 42, line 24, Claim 22: after "19" insert --which--

Signed and Sealed this

Second Day of March, 1999

Attest:

Q. TODD DICKINSON

Attesting Officer

Acting Commissioner of Patents and Trademarks